United States Patent
Palushi et al.

(10) Patent No.: US 11,696,775 B2
(45) Date of Patent: Jul. 11, 2023

(54) METHOD OF TREATING DEVIATED NASAL SEPTUM, ENLARGED NASAL TURBINATE, OR MUCOSAL HYPERTROPHY

(71) Applicant: Acclarent, Inc., Irvine, CA (US)

(72) Inventors: Jetmir Palushi, Irvine, CA (US); Fatemeh Akbarian, Rancho Palos Verdes, CA (US); Athanasios Papadakis, Newport Beach, CA (US); Ehsan Shameli, Irvine, CA (US); William J. Kane, Newport Coast, CA (US); Henry F. Salazar, Pico Rivera, CA (US); Julie M. Taylor, Yorba Linda, CA (US); Marc Dean, Fort Worth, TX (US)

(73) Assignee: Acclarent, Inc., Irvine, CA (US)

( * ) Notice: Subject to any disclaimer, the term of this patent is extended or adjusted under 35 U.S.C. 154(b) by 99 days.

(21) Appl. No.: 16/396,846

(22) Filed: Apr. 29, 2019

(65) Prior Publication Data
US 2019/0357927 A1 Nov. 28, 2019

Related U.S. Application Data

(60) Provisional application No. 62/674,767, filed on May 22, 2018.

(51) Int. Cl.
*A61B 17/24* (2006.01)
*A61M 29/02* (2006.01)
(Continued)

(52) U.S. Cl.
CPC ............ *A61B 17/24* (2013.01); *A61M 29/02* (2013.01); *A61B 2017/00557* (2013.01);
(Continued)

(58) Field of Classification Search
CPC .......... A61M 2210/0681; A61M 29/02; A61M 25/1011; A61M 2029/025;
(Continued)

(56) References Cited

U.S. PATENT DOCUMENTS

| | | | |
|---|---|---|---|
| 2005/0240147 A1* | 10/2005 | Makower | A61B 17/3201 604/96.01 |
| 2008/0125805 A1* | 5/2008 | Mische | A61B 17/7258 604/103.02 |

(Continued)

OTHER PUBLICATIONS

International Search Report and Written Opinion dated Aug. 1, 2019 for Application No. PCT/IB2019/053634, 11 pgs.
(Continued)

*Primary Examiner* — Kathleen S Holwerda
*Assistant Examiner* — Lauren Dubose
(74) *Attorney, Agent, or Firm* — Frost Brown Todd LLP

(57) ABSTRACT

A method includes inserting a first dilation catheter into a first nostril of a patient. A first dilator of the first dilation catheter is positioned between the nasal septum of the patient and the turbinate of the patient. The first dilator is expanded, thereby remodeling one or more of the nasal septum, the turbinate, or mucosal tissue of the patient. The first dilation catheter is removed from the nostril of the patient. A second dilation catheter may be inserted into a second nostril of the patient. A dilator of the second dilation catheter may provide an opposing force on the nasal septum to prevent over-medialization of the nasal septum.

20 Claims, 25 Drawing Sheets

(51) Int. Cl.
*A61B 17/00* (2006.01)
*A61M 25/10* (2013.01)

(52) U.S. Cl.
CPC ............. *A61B 2017/246* (2013.01); *A61M 2025/1086* (2013.01); *A61M 2210/0618* (2013.01)

(58) Field of Classification Search
CPC ...... A61M 2025/1086; A61M 25/0023; A61M 2210/0618; A61F 5/08; A61B 17/24; A61B 2017/246; A61B 2017/248; A61B 2017/00557
USPC .................................................. 606/196, 199
See application file for complete search history.

(56) References Cited

U.S. PATENT DOCUMENTS

| | | | |
|---|---|---|---|
| 2008/0215018 A1* | 9/2008 | Duffy | A61F 2/954 604/284 |
| 2012/0259217 A1* | 10/2012 | Gerrans | A61M 25/10181 600/435 |
| 2014/0277043 A1* | 9/2014 | Jenkins | A61B 34/30 134/6 |
| 2014/0277071 A1* | 9/2014 | Wu | A61M 29/02 606/196 |
| 2015/0080935 A1 | 3/2015 | Dillard | |
| 2017/0360511 A1* | 12/2017 | Smith | A61B 5/4824 |
| 2018/0325422 A1* | 11/2018 | Sokol | A62B 7/10 |
| 2018/0344378 A1* | 12/2018 | Wolf | A61B 18/085 |

OTHER PUBLICATIONS

U.S. Appl. No. 62/974,767, entitled "Method of Treating Deviated Nasal Septum, Enlarged Nasal Turbinate, or Mucosal Hypertrophy," filed May 22, 2018.

* cited by examiner

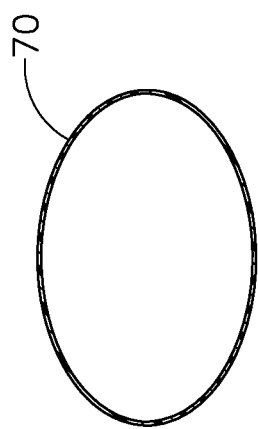
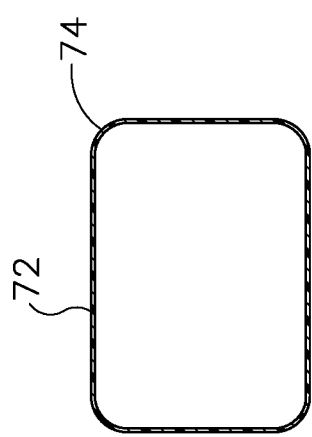
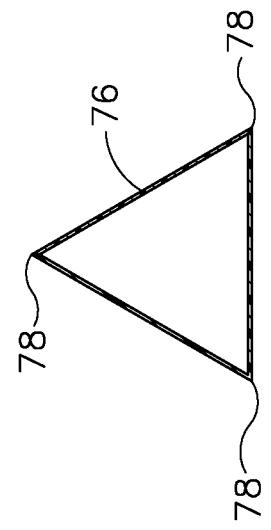

METHOD OF TREATING DEVIATED NASAL SEPTUM, ENLARGED NASAL TURBINATE, OR MUCOSAL HYPERTROPHY

PRIORITY

This application claims the benefit of U.S. Provisional Patent Application No. 62/674,767, entitled "Method of Treating Deviated Nasal Septum, Enlarged Nasal Turbinate, or Mucosal Hypertrophy," filed May 22, 2018, which is incorporated by reference herein in its entirety.

BACKGROUND

A human nasal cavity includes a nasal septum and a set of turbinates. A turbinate (or nasal conchae) is a long, narrow and curled bone shelf which protrudes medially into the nasal passages. Turbinates divide the nasal airway into three (or in some cases four) groove-like air passages (i.e., nasi meatae) and are responsible for forcing inhaled air to flow in a steady, regular pattern around the largest possible surface of cilia, and climate controlling tissue of the nasal passage. Turbinates are composed of pseudo-stratified columnar ciliated respiratory epithelium with a thick, vascular and erectile glandular tissue layer. The turbinates are located laterally in the nasal cavities, curling medially and downwardly into the nasal airway. In many cases, there are three pairs of turbinates—superior turbinates, middle turbinates, and inferior turbinates. In some cases, there is an additional pair of turbinates known as the supreme turbinates. Each turbinate pair is composed of one turbinate in either side of the nasal cavity, divided by the nasal septum.

The nasal septum is formed of bone and cartilage, with an exterior lining of mucosal tissue. When the cartilage or bone is off-center (i.e., deviated laterally) or crooked, the condition may be referred to as a deviated septum. A deviated septum may come into close proximity to an adjacent turbinate, or even engage an adjacent turbinate, and thereby create a restriction or blockage in the nasal passageway, which may lead to breathing difficulties, bleeding, pain, and/or other undesirable conditions in a patient. It may therefore be desirable to treat a deviated septum to ameliorate and prevent such undesirable conditions.

Some conventional approaches to addressing a deviated nasal septum may include a septoplasty procedure. A septoplasty procedure may include making an incision in the mucosal tissue of the nasal septum, removing at least a portion of the nasal septum, straightening the removed nasal septum, and then inserting the straightened nasal septum into the mucosal tissue. Such an approach may be considered aggressive and time consuming. It may be desirable to address a deviated nasal septum in a manner that is less invasive than a conventional septoplasty procedure, under local anesthesia in a doctor's office. It may also be desirable to address a deviated nasal septum in a manner that does not require the complexity and skill associated with a septoplasty procedure.

Some patients may also suffer from a turbinate that has become enlarged due to inflammation or infection. Like a deviated nasal septum, an enlarged turbinate may lead to breathing difficulties, bleeding, pain, and/or other undesirable conditions in a patient. Some conventional approaches to addressing an enlarged turbinate may include reducing the turbinate by using scissors to cut the turbinate, using forceps to crush the turbinate, or using energy to desiccate the turbinate. It may be desirable to address an enlarged turbinate using less invasive methods that require less complexity and skill than the turbinate reduction procedures noted above.

Some patients may also suffer from a hypertrophy of mucosal tissue in the nasal cavity. In some instances, the collapsed mucosal tissue may obstruct air flowing through the nasal cavity. Some conventional approaches to addressing collapsed mucosal tissue may include resecting the collapsed mucosal tissue to provide a clear passage air flow through the nasal cavity. It may be desirable to address collapsed mucosal tissue in a nasal cavity using less invasive methods that require less complexity and skill than the mucosa resection procedures noted above.

While several systems and methods have been made and used to treat a deviated nasal septum and other anatomical structures within the nasal cavity, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 12A depicts a cross-sectional rear view of the dilator of FIG. 11, taken along line 12-12 of FIG. 11;

FIG. 12B depicts an alternative cross-sectional rear view of the dilator of FIG. 11, taken along line 12-12 of FIG. 11; and FIG. 12C depicts another alternative cross-sectional rear view of the dilator of FIG. 11, taken along line 12-12 of FIG. 11.

Figure 1A:
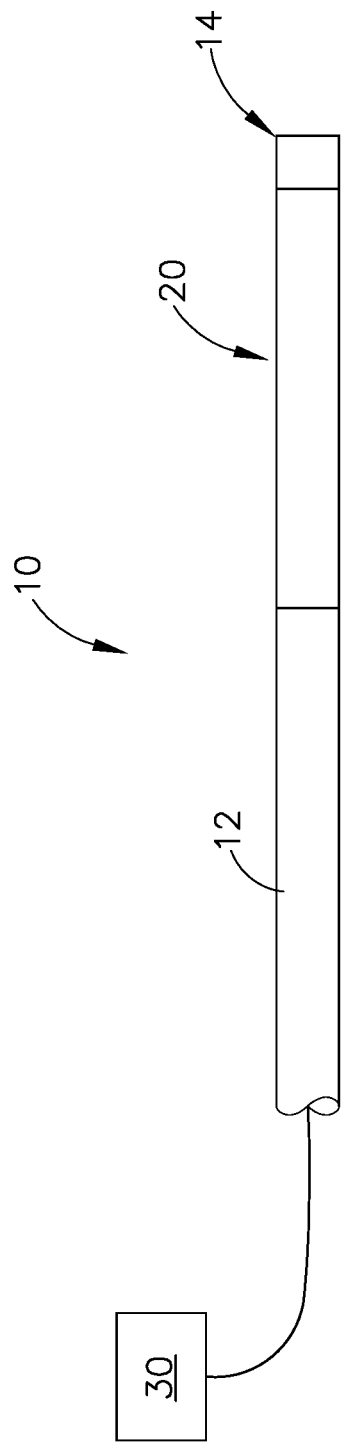
FIG. 1A depicts a side schematic view of an exemplary dilation catheter, with a dilator of the dilation catheter in a non-expanded state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Catheter

Figure 1B:
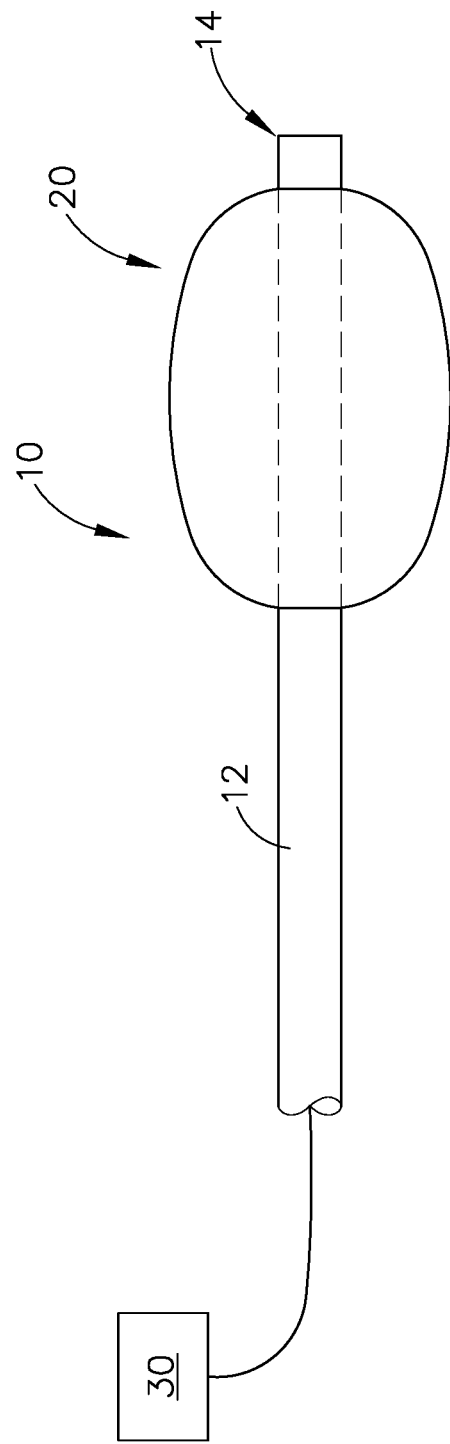
FIG. 1B depicts a side schematic view of the dilation catheter of FIG. 1A, with the dilator in an expanded state.

FIGS. 1A-1B show a distal portion of an exemplary dilation catheter (10). Dilation catheter (10) of this example includes an elongate shaft (12), with a dilator (20) positioned near the distal end (14) of shaft (12). Shaft (12) of the present example is generally flexible, such that distal end (14) and other portions of shaft (12) may bend away from a straight longitudinal axis of shaft (12). However, shaft (12) also has sufficient column strength to enable a distal portion of shaft (12) to be pushed into a nasal cavity of a patient (e.g., as described below), without causing shaft (12) to substantially buckle. Various suitable materials that may be used to form shaft (12) will be apparent to those of ordinary skill in the art in view of the teachings herein.

Dilator (20) of the present example comprises an inflatable balloon. Dilator (20) is in fluid communication with a source (30) of inflation fluid (e.g., saline). The inflation fluid may thus be communicated from source (30) to dilator (20) to transition dilator (20) from a non-expanded state (FIG. 1A) to an expanded state (FIG. 1B); and back from dilator (20) to source (30) to transition dilator (20) from the expanded state (FIG. 1B) back to the non-expanded state (FIG. 1A). In some versions, the balloon forming dilator (20) comprises an extensible material, such that dilator (20) is resiliently biased to assume the non-expanded configuration of FIG. 1A. In some other versions, the balloon forming dilator comprises a flexible yet non-extensible material (e.g., mylar). In some other versions, dilator (20) is in the form of a mechanically expandable element that does not require fluid to transition from a non-expanded state to an expanded state. In the present example, dilator (20) is configured to achieve an outer diameter of approximately 16 mm when dilator (20) is in the fully expanded state. By way of further example only, dilator (20) may be configured to achieve an outer diameter between approximately 10 mm and approximately 16 mm when dilator (20) is in the fully expanded state.

Shaft (12) of the present example further includes a lumen (not shown) providing a pathway for fluid communication between fluid source (30) and dilator (20). In some versions, shaft (12) also includes a separate lumen that is configured to slidably receive a guidewire. In addition, or in the alternative, shaft (12) may include one or more lumens that is/are configured to provide ventilation, suction, irrigation, medication, or other effects through distal end (14). Other features an operabilities that may be incorporated into dilation catheter (10) will be apparent to those of ordinary skill in the art in view of the teachings herein.

II. Exemplary Method of Treating a Deviated Nasal Septum

Figure 2A:
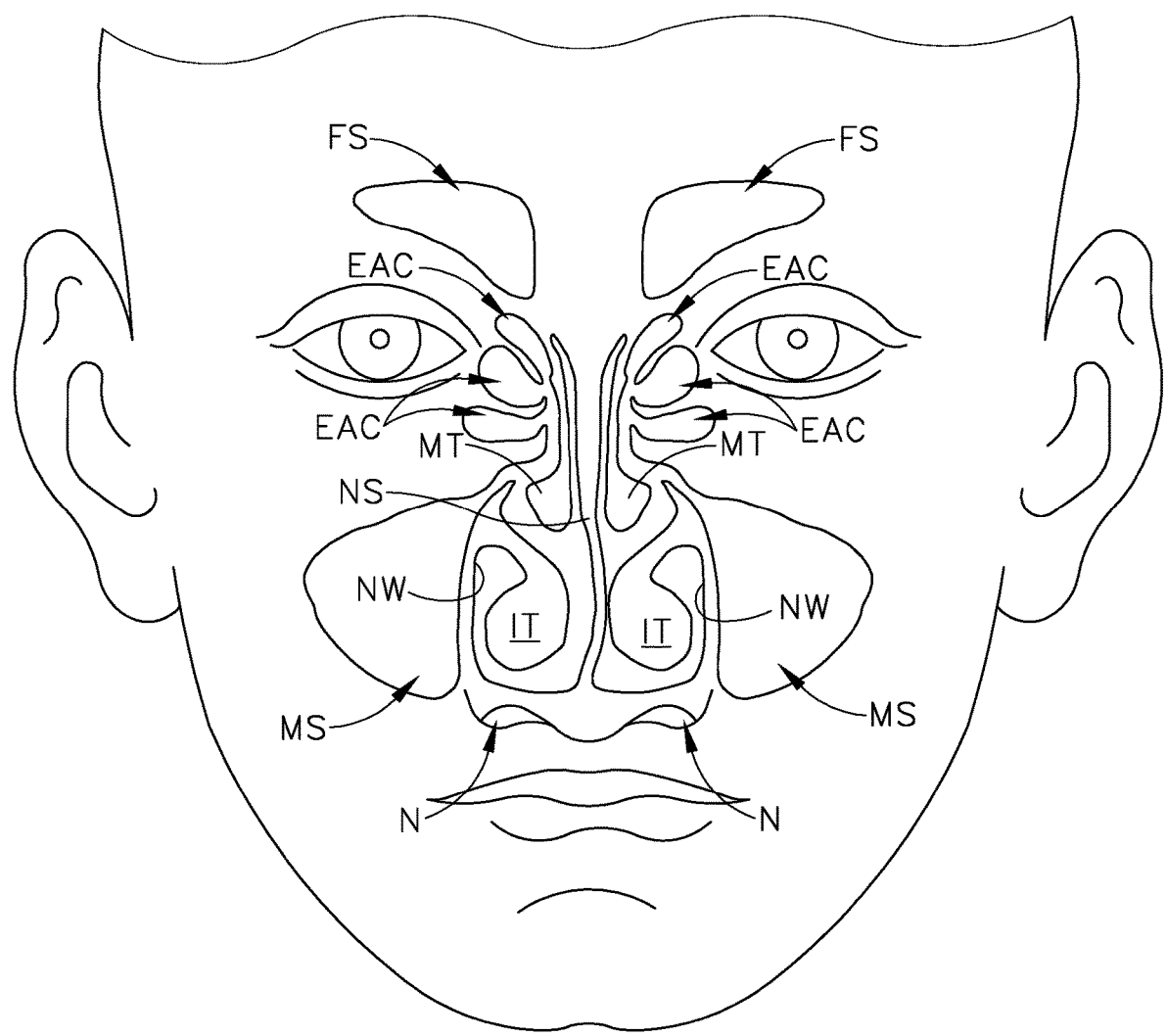
FIG. 2A depicts a schematic view, along a coronal plane, of anatomical structures associated with a nasal cavity of a patient, including a nasal septum in a deviated state, before a first exemplary treatment procedure.
Figure 3A:
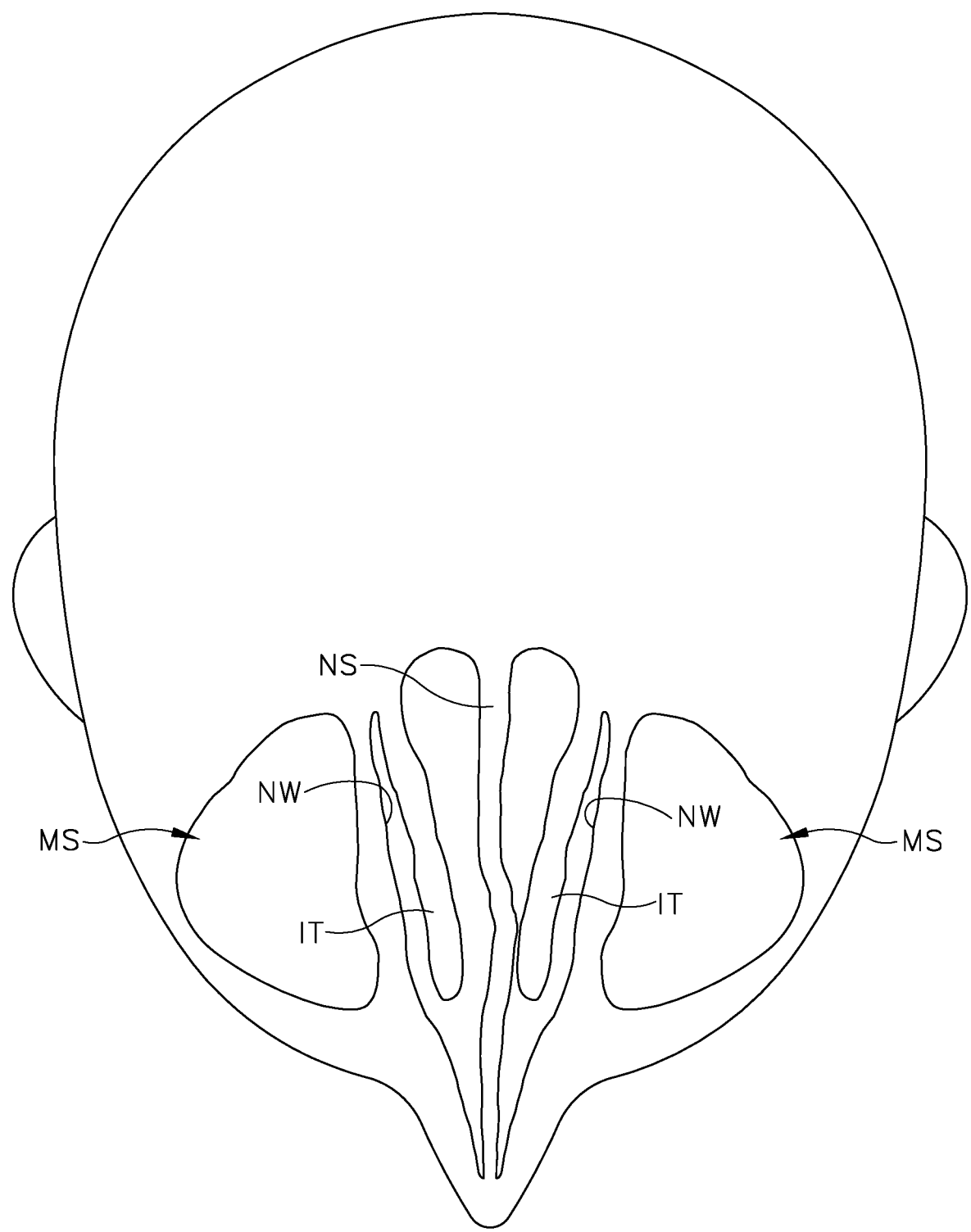
FIG. 3A depicts a schematic view, along an axial plane, of anatomical structures associated with a nasal cavity of a patient, including the nasal septum in the deviated state of FIG. 2A, before the first exemplary treatment procedure.

FIGS. 2A and 3A show various anatomical structures associated with a nasal cavity of a patient. These structures include a pair of frontal sinus cavities (FS), a set of ethmoid air cells (EAC), a pair of maxillary sinus cavities (MS), a pair of middle turbinates (MT), a pair of inferior turbinates (IT), and a nasal septum (NS) separating the members of each pair. Due to the location of the cross-sectional plane of the view in FIGS. 2A and 3A, the superior turbinates are not shown. As shown in FIGS. 2A and 3A, the nasal septum (NS) is deviated laterally against on inferior turbinate (IT) in the patient. As noted above, this condition may cause a restriction or blockage in the nasal passageway, which may lead to breathing difficulties, bleeding, pain, and/or other undesirable conditions in the patient.

Figure 2B:
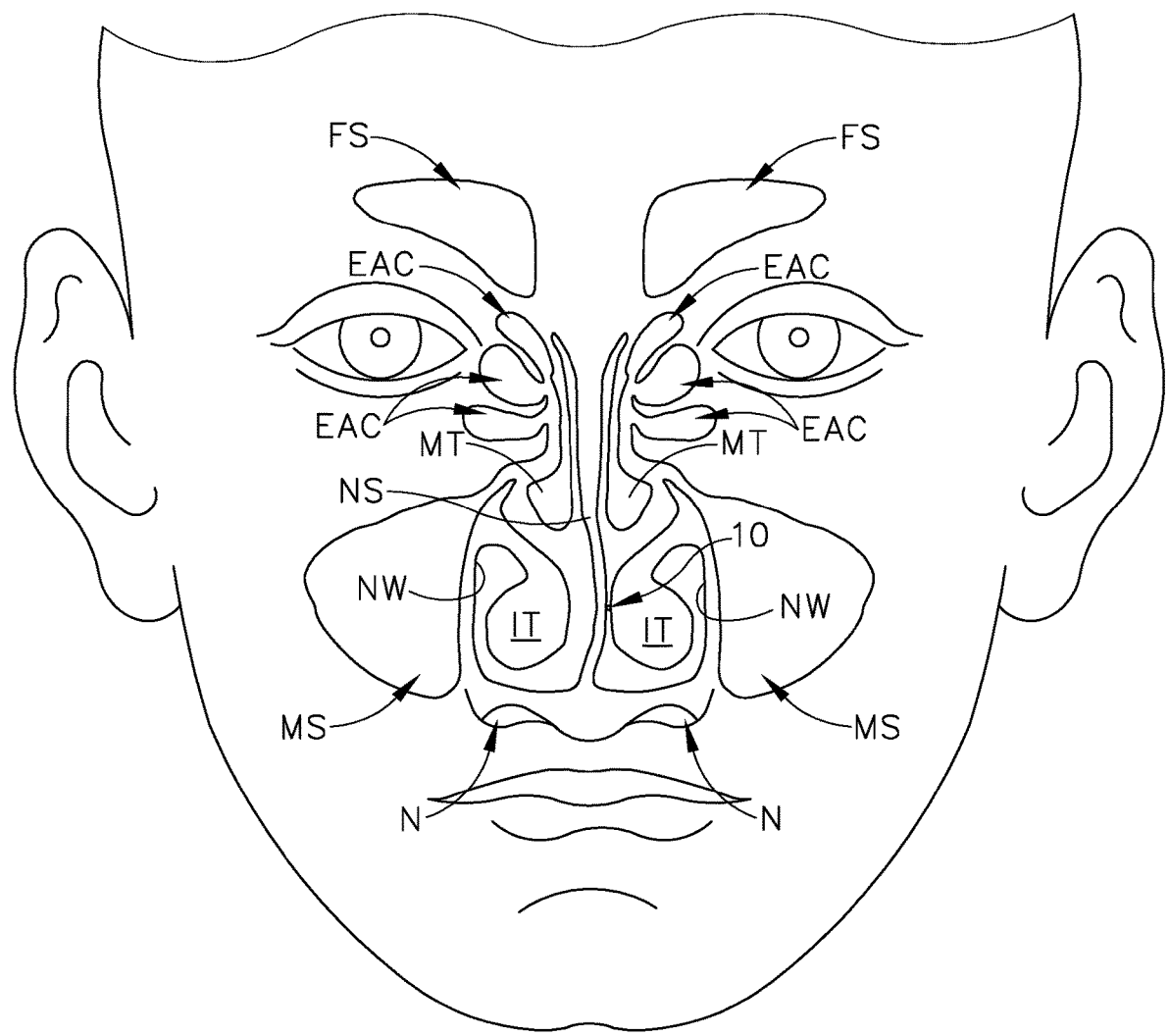
FIG. 2B depicts a schematic view, along a coronal plane, of the anatomical structures associated with the nasal cavity of the patient of FIG. 2A, with a distal portion of the dilation catheter of FIG. 1A inserted through a nostril of the patient, and with the dilator of the dilation catheter in the non-expanded state.
Figure 3B:
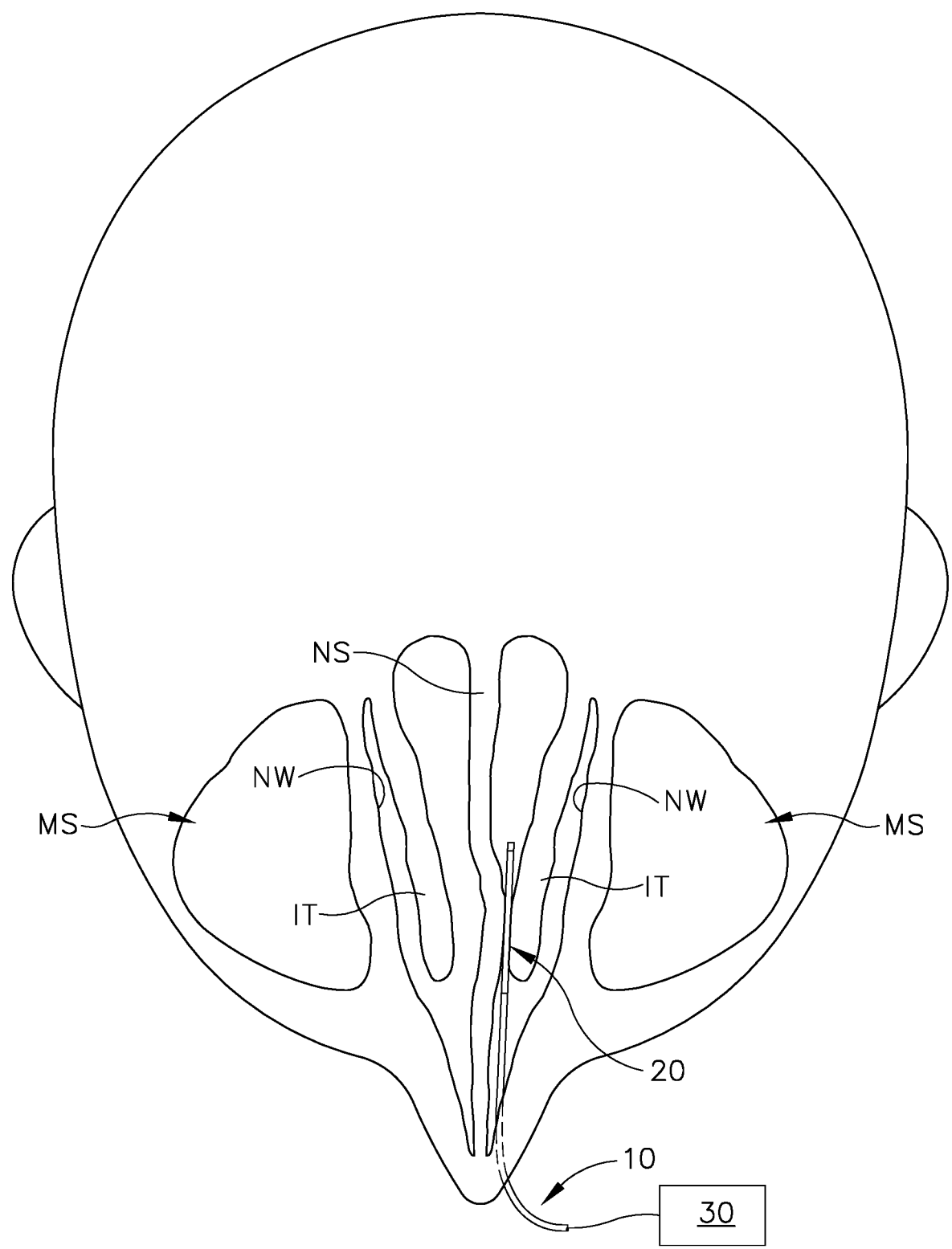
FIG. 3B depicts a schematic view, along an axial plane, of the anatomical structures associated with the nasal cavity of the patient of FIG. 3A, with the distal portion of the dilation catheter of FIG. 1A inserted through a nostril of the patient, and with the dilator of the dilation catheter in the non-expanded state.

FIGS. 2B and 3B show an initial step in an exemplary procedure to treat the deviated nasal septum (NS) of FIGS. 2A and 3A. In particular, the distal portion of dilation catheter (10) is inserted into a nostril (N) of the patient, on the side where the nasal septum (NS) is deviated into the inferior turbinate (IT). Dilator (20) is in a non-expanded state while dilation catheter (10) is inserted into position. Dilation catheter (10) is inserted to a position where dilator (20) is interposed between the deviated portion of the nasal septum (NS) and the inferior turbinate (IT). Shaft (12) of dilation catheter (10) provides sufficient column strength to overcome any frictional resistance provided between the nasal septum (NS) and the inferior turbinate (IT), thereby enabling dilator (20) to be positioned between the nasal septum (NS) and the inferior turbinate (IT) without causing substantial buckling in shaft (12).

In some variations, a guidewire (not shown) is first positioned between the nasal septum (NS) and the inferior turbinate (IT); and then dilation catheter (10) is advanced along the guidewire to position dilator (20) between the nasal septum (NS) and the inferior turbinate (IT). As another merely illustrative example, a rigid or malleable guide catheter may first be positioned at or in the nostril (N); and then dilation catheter (10) may be advanced through the guide catheter to position dilator (20) between the nasal septum (NS) and the inferior turbinate (IT). Other suitable devices and techniques that may be used to achieve the positioning shown in FIGS. 2B and 3B will be apparent to those of ordinary skill in the art in view of the teachings herein.

Figure 2C:
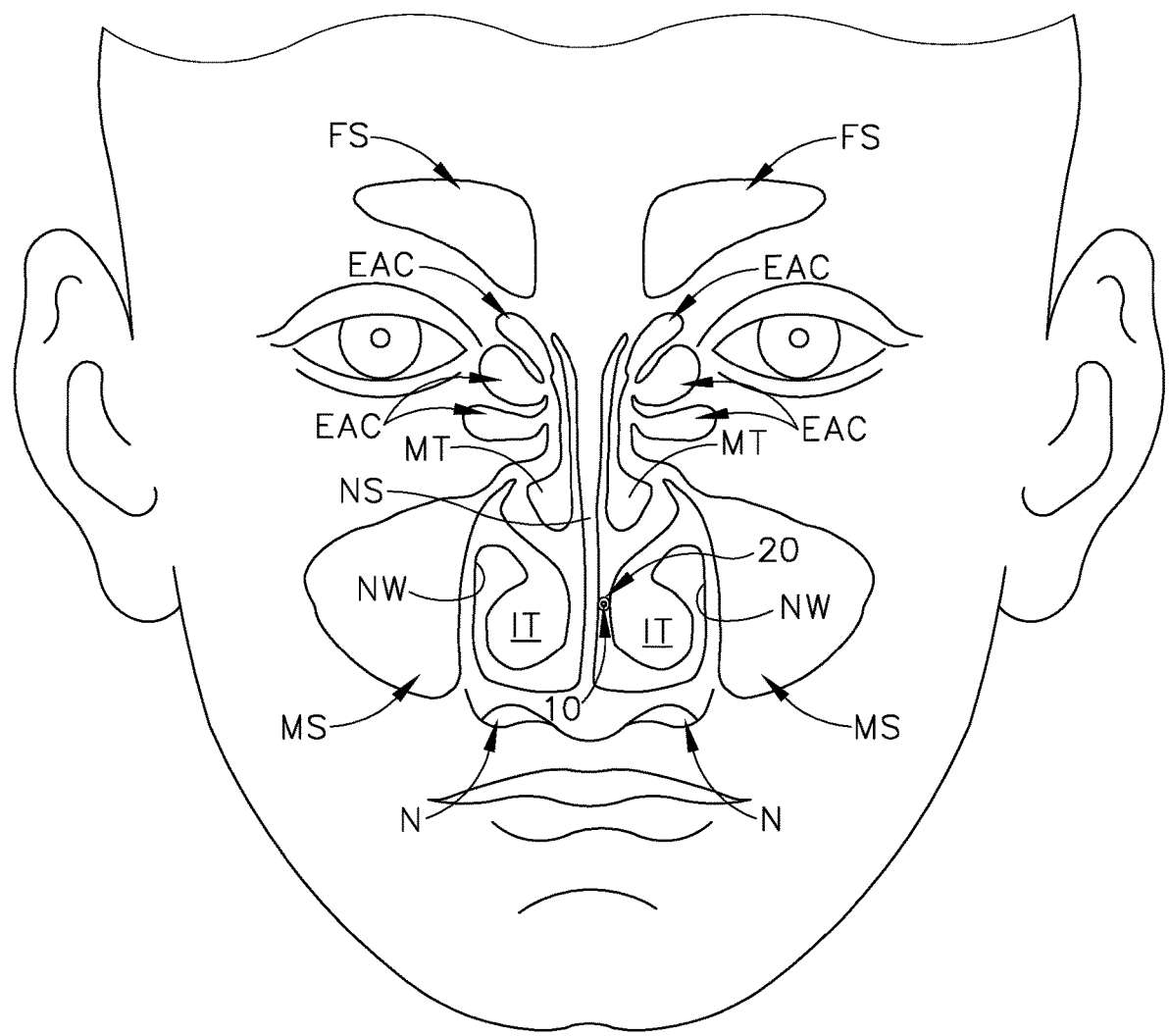
FIG. 2C depicts a schematic view, along a coronal plane, of the anatomical structures associated with the nasal cavity of the patient of FIG. 2A, with the distal portion of the dilation catheter of FIG. 1A inserted through a nostril of the patient, and with the dilator of the dilation catheter in the expanded state.
Figure 2D:
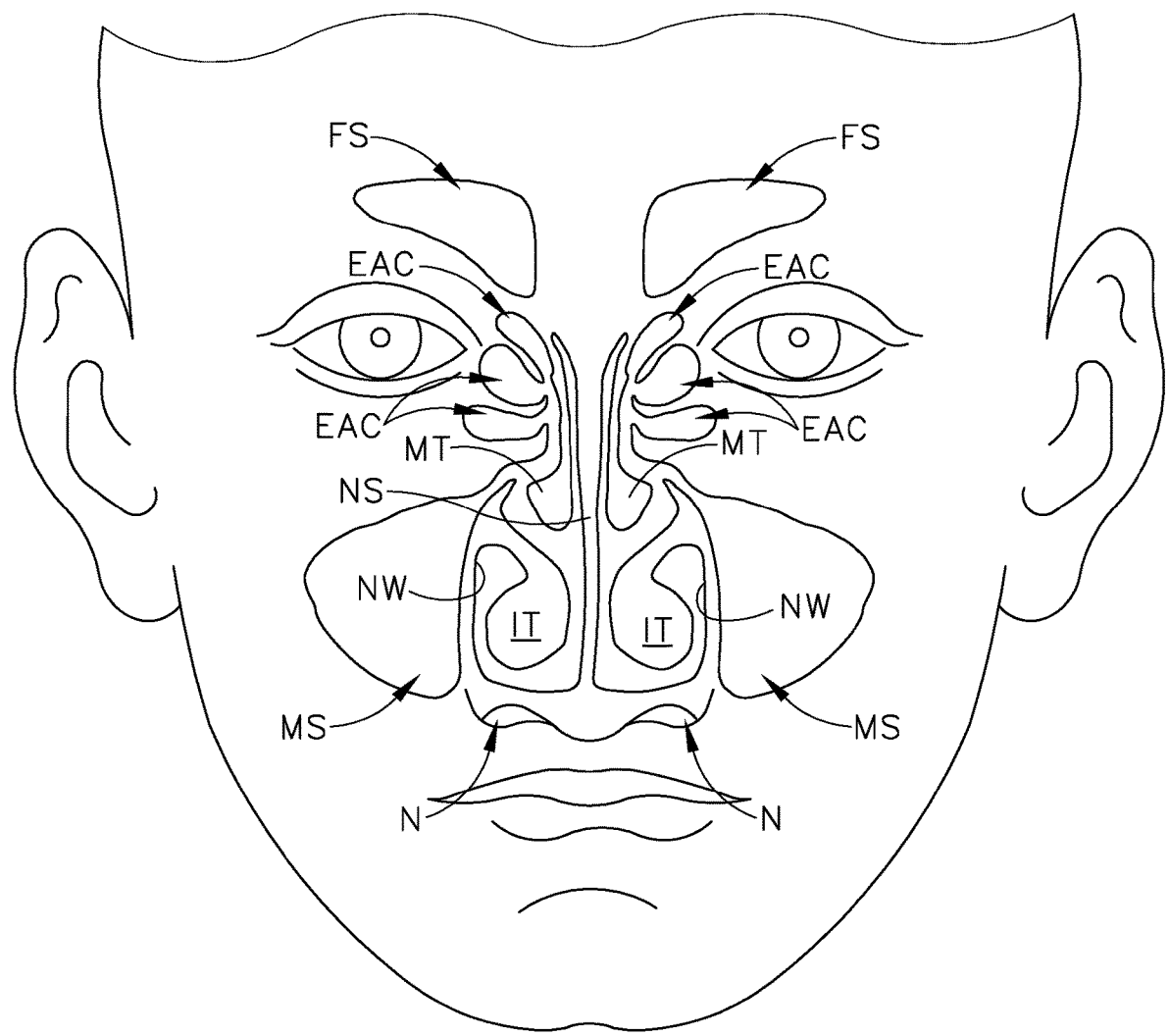
FIG. 2D depicts a schematic view, along a coronal plane, of the anatomical structures associated with the nasal cavity of the patient of FIG. 2A, with the dilation catheter of FIG. 1A removed from the patient, and with the nasal septum in a non-deviated state.
Figure 3C:
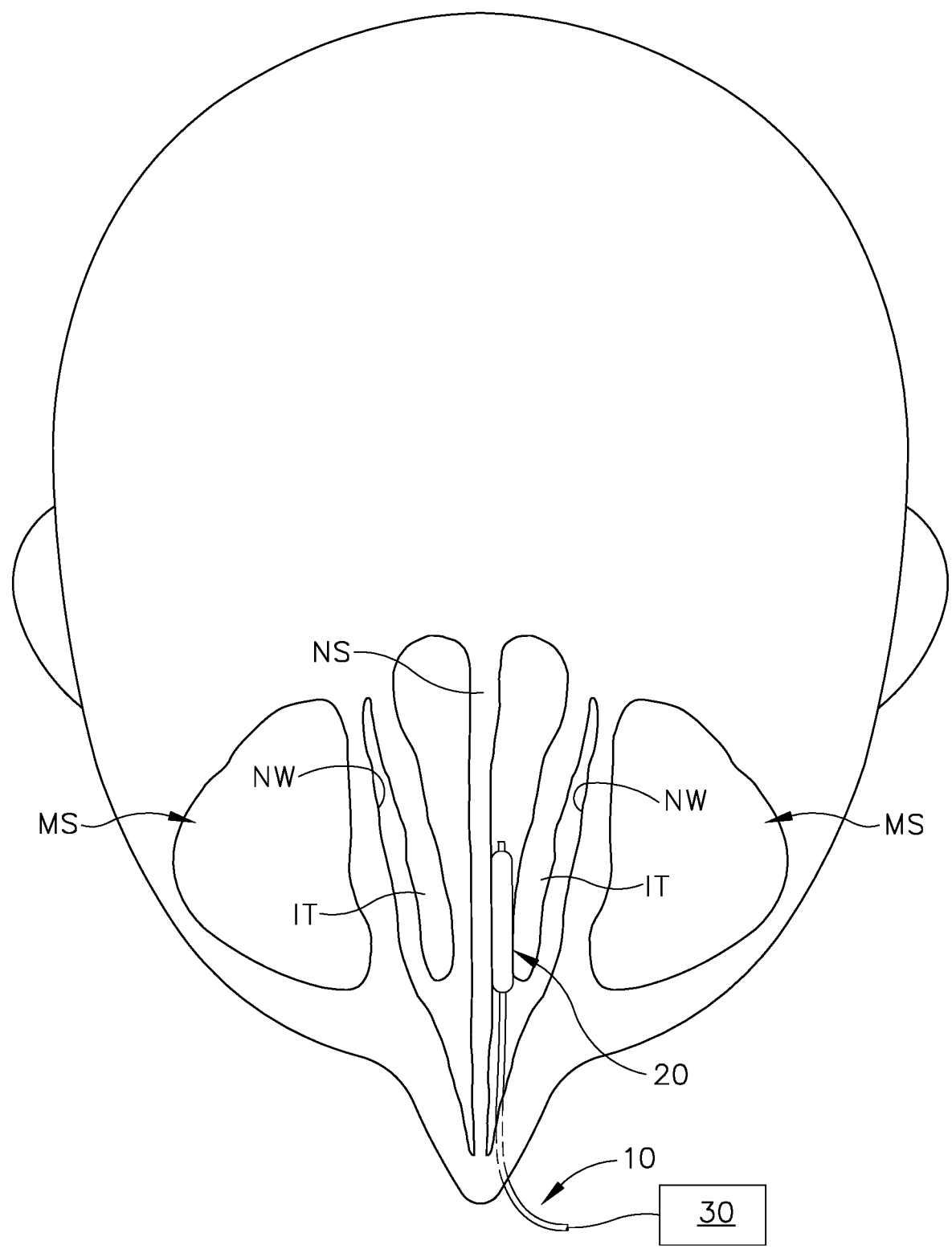
FIG. 3C depicts a schematic view, along an axial plane, of the anatomical structures associated with the nasal cavity of the patient of FIG. 3A, with the distal portion of the dilation catheter of FIG. 1A inserted through a nostril of the patient, and with the dilator of the dilation catheter in the expanded state.
Figure 3D:
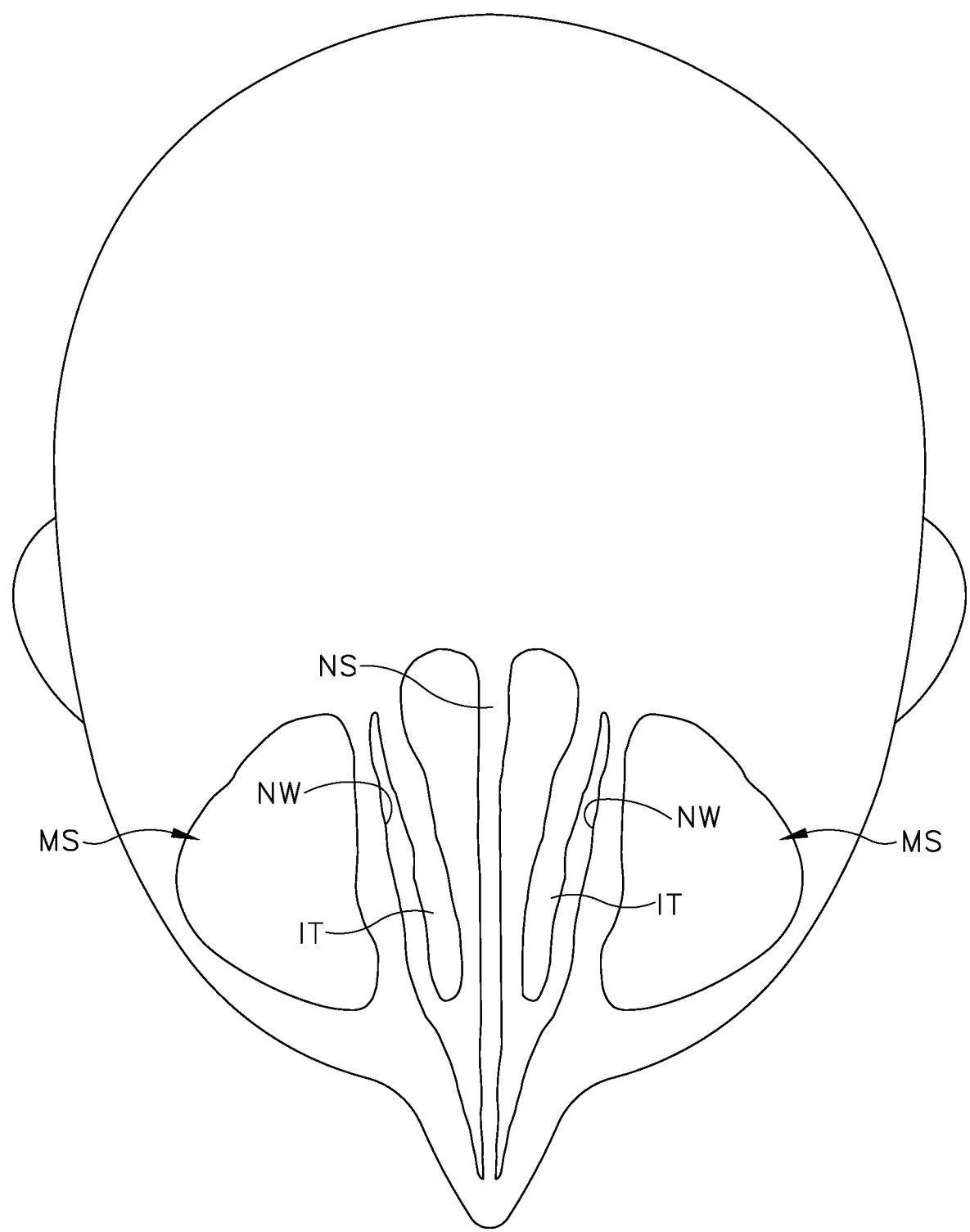
FIG. 3D depicts a schematic view, along an axial plane, of the anatomical structures associated with the nasal cavity of the patient of FIG. 3A, with the dilation catheter of FIG. 1A removed from the patient, and with the nasal septum in a non-deviated state.

Once dilator (20) has been suitably positioned between the nasal septum (NS) and the inferior turbinate (IT), inflation fluid is driven from fluid source (30) to dilator (20), thereby expanding dilator (20) to the expanded state shown in FIGS. 2C and 3C. As dilator (20) expands, dilator (20) urges the nasal septum (NS) medially, thereby substantially straightening the nasal septum (NS). As the nasal septum (NS) is urged medially, the bone in the nasal septum (NS) may fracture and/or the cartilage in the nasal septum (NS) may plastically deform, such that the medially urged nasal septum (NS) is effectively remodeled and maintains a substantially straight configuration after dilation catheter (10) is removed as shown in FIGS. 2D and 3D.

In the present example, during the stage shown in FIGS. 2C and 3C, the adjacent inferior turbinate (IT) provides at least some degree of a mechanical ground for dilator (20), enabling the expanded dilator (20) to move the nasal septum (NS) medially. In some scenarios, the adjacent inferior turbinate (IT) is urged laterally (and, in some cases, at least partially fractured) to at least some degree when dilator (20) is expanded. In such scenarios, the inferior turbinate (IT)

may still eventually engage the adjacent lateral nasal wall (NW), such that the laterally urged inferior turbinate (IT) cooperates with the adjacent lateral nasal wall (NW) to provide a mechanical ground for the expanded dilator (20). In addition to remodeling the nasal septum (NS) as described above, the expansion of dilator (20) may further remodel the adjacent inferior turbinate (IT) to some degree. For instance, the expanding dilator (20) may fracture at least some of the bone forming the inferior turbinate (IT), such that the inferior turbinate (IT) remains at least partially lateralized after dilation catheter (10) is removed from the nasal cavity. Thus, while FIGS. 2D and 3D only shows the nasal septum (NS) being remodeled at the end of the procedure of FIGS. 2A-2D and 3A-3D, the inferior turbinate (IT) may also be remodeled at the end of the procedure in some scenarios. Moreover, the mucosa of the inferior turbinate (IT) may be crushed during the procedure.

Figure 4A:
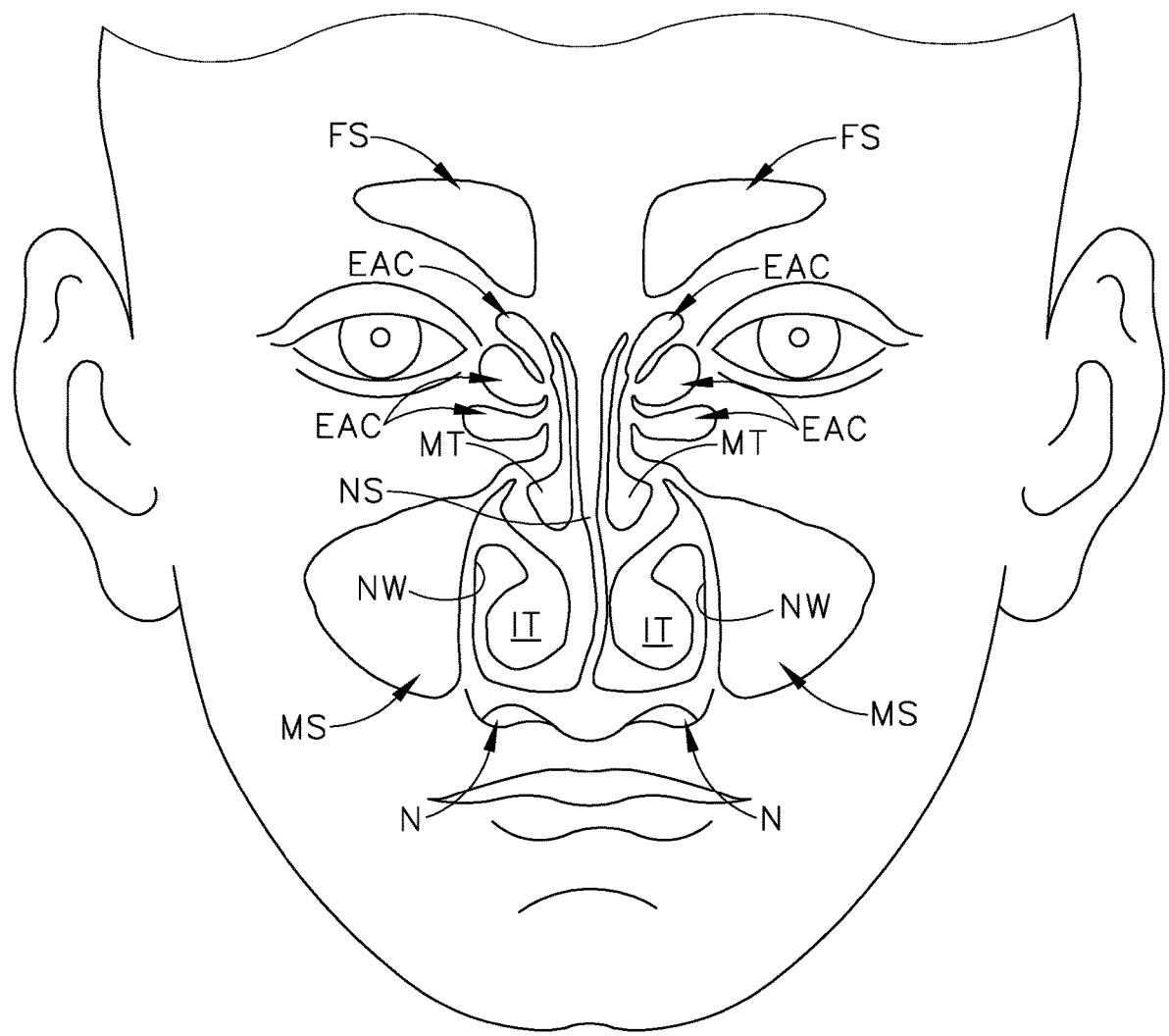
FIG. 4A depicts a schematic view, along a coronal plane, of anatomical structures associated with a nasal cavity of a patient, including a nasal septum in a deviated state, before a second exemplary treatment procedure.

FIGS. 4A-5D show an exemplary alternative procedure that may be used to treat a deviated nasal septum (NS). As shown in FIGS. 4A and 5A, the patient has the same deviated nasal septum (NS) state as the patient shown in FIGS. 2A and 3A. In this alternative treatment procedure, two dilation catheters (10) are used. As shown in FIGS. 4B and 5B, a dilation catheter (10) is inserted into each nostril (N), with both dilators (20) in the non-expanded state. The distal portion of a first dilation catheter (10) is inserted into the nostril (N) of the patient on the side where the nasal septum (NS) is deviated into the inferior turbinate (IT). This first dilation catheter (10) is inserted to a position where dilator (20) is interposed between the deviated portion of the nasal septum (NS) and the inferior turbinate (IT). The distal portion of the second dilation catheter (10) is inserted into the other nostril (N), to a depth corresponding to the insertion depth of the first dilation catheter (10). Both dilation catheters (10) are thus correspondingly positioned on opposite sides of the nasal septum (NS). As noted above, guidewires, guide catheters, and/or any other suitable devices or techniques may be used to assist in achieving the positioning shown in FIGS. 4B and 5B.

Figure 4B:
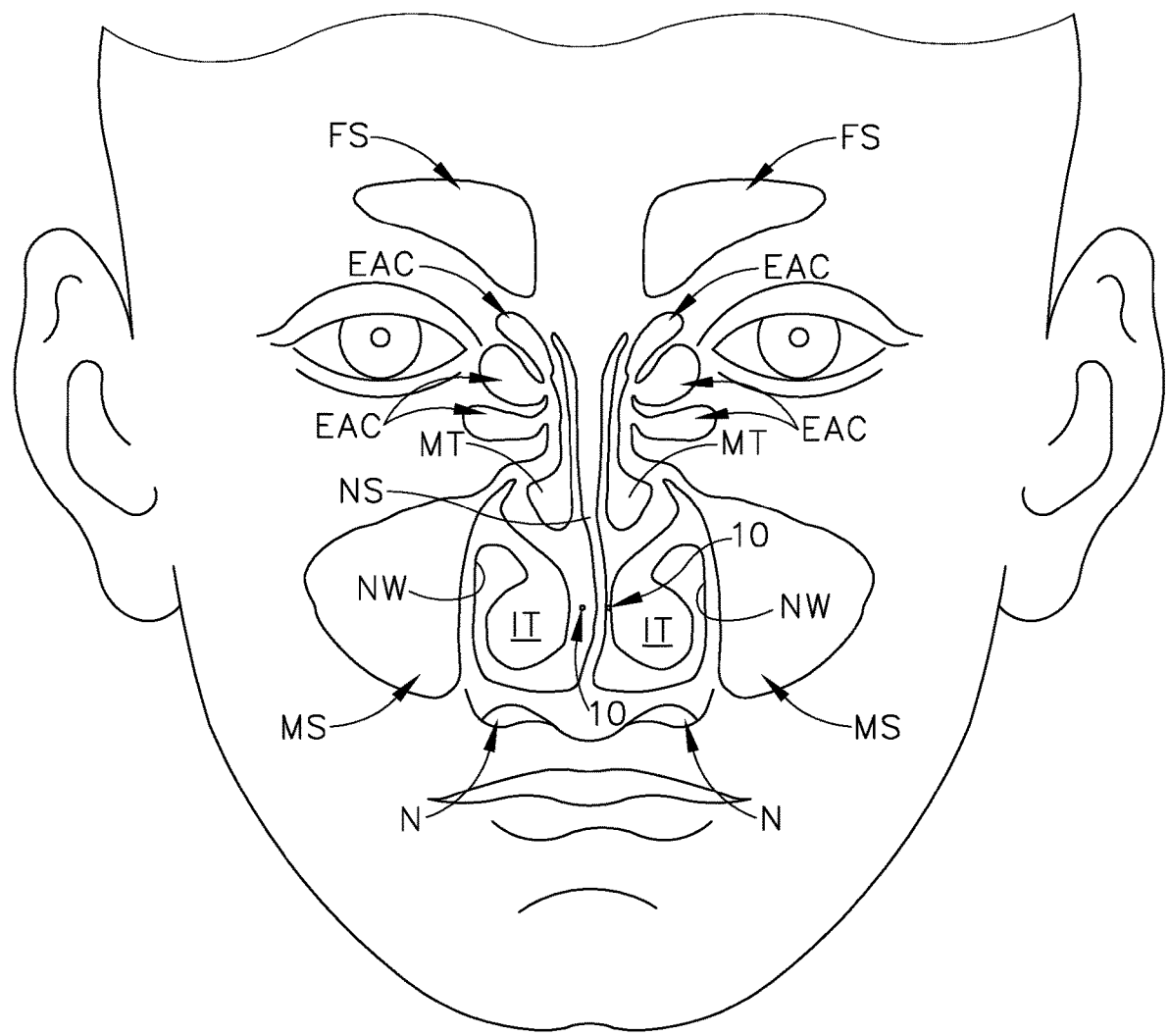
FIG. 4B depicts a schematic view, along a coronal plane, of the anatomical structures associated with the nasal cavity of the patient of FIG. 4A, with distal portions of two dilation catheters inserted through respective nostrils of the patient, and with the dilator of each dilation catheter in the non-expanded state.
Figure 4C:
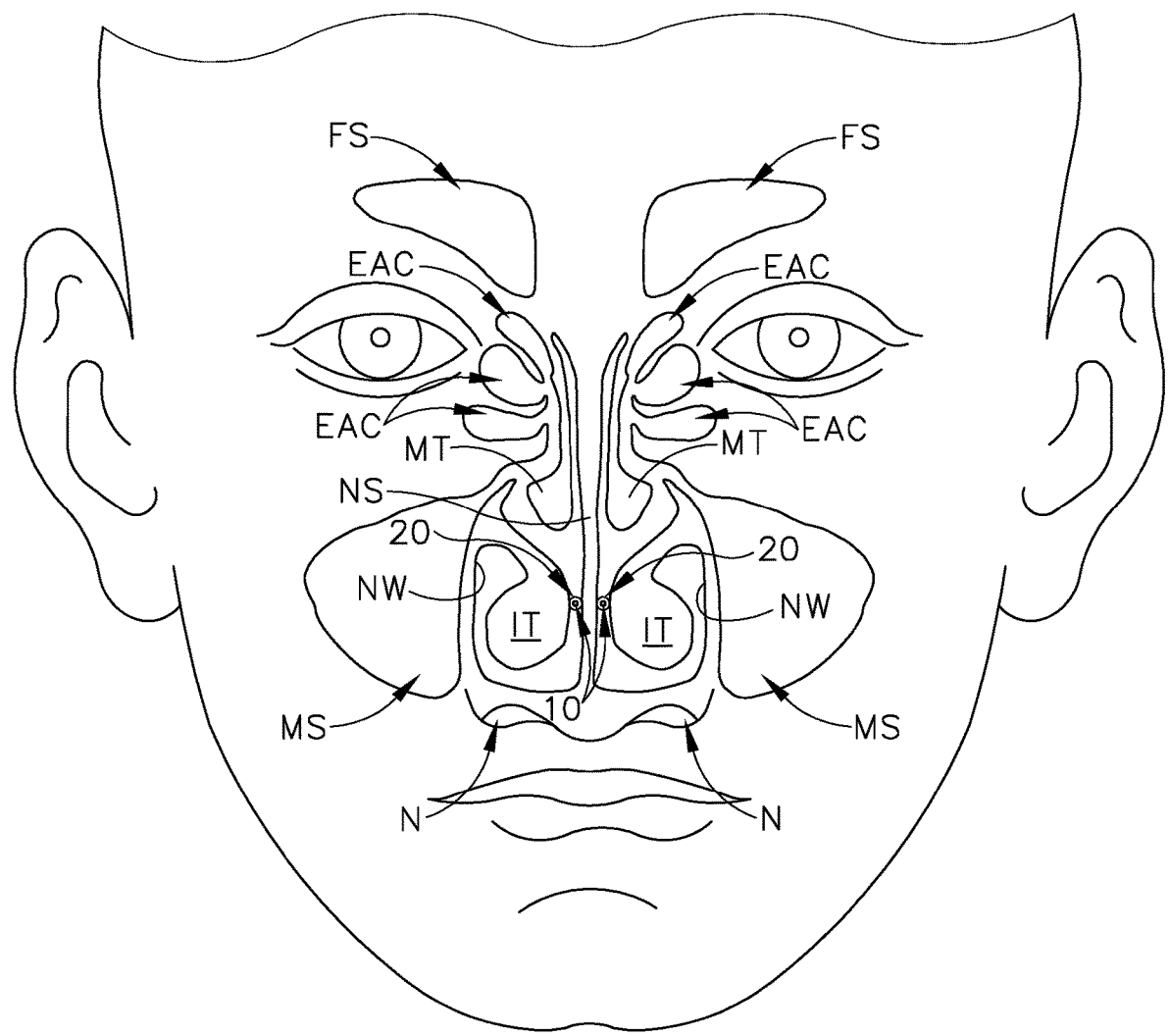
FIG. 4C depicts a schematic view, along a coronal plane, of the anatomical structures associated with the nasal cavity of the patient of FIG. 4A, with distal portions of two dilation catheters inserted through respective nostrils of the patient, and with the dilator of each dilation catheter in the expanded state.
Figure 4D:
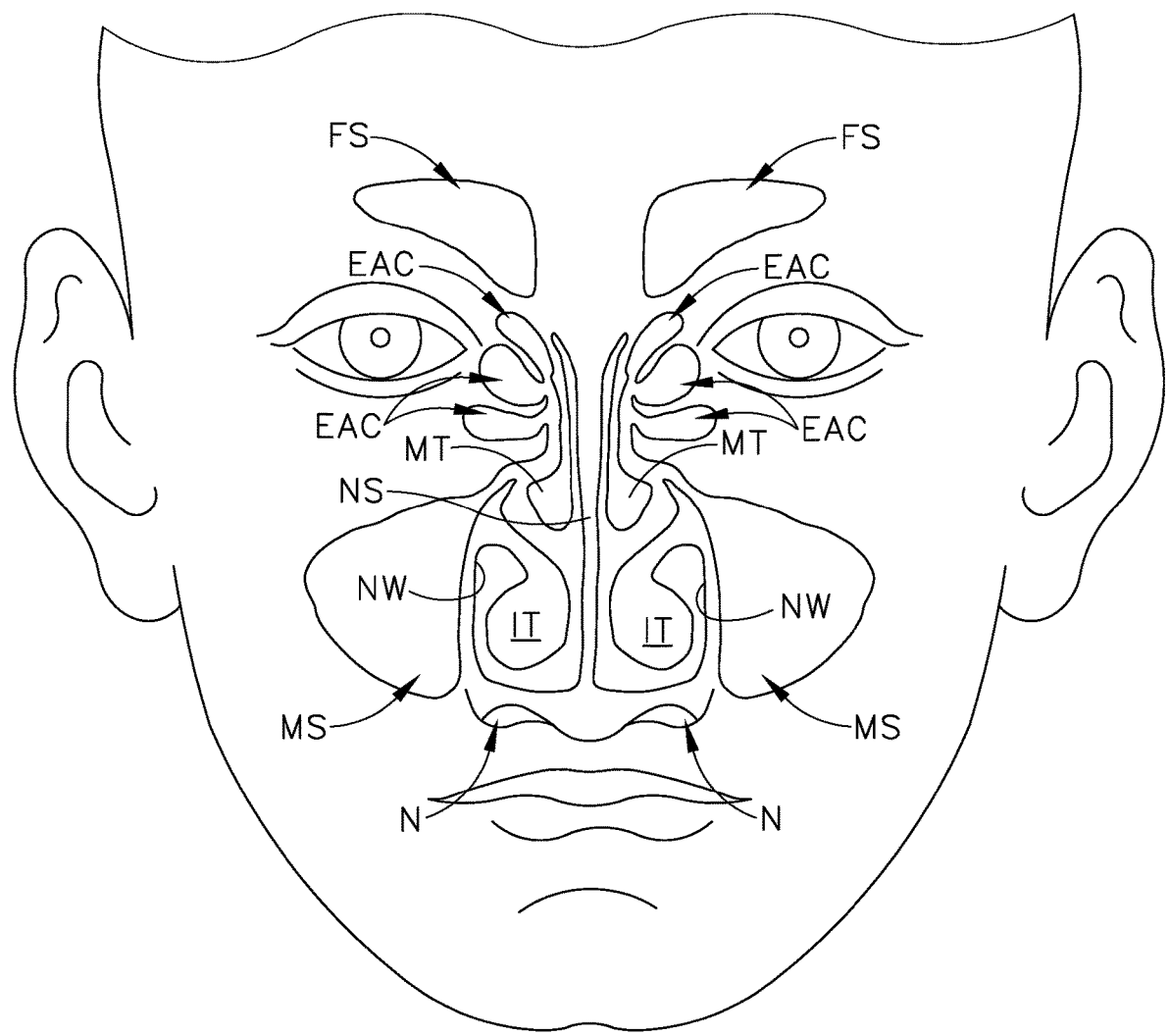
FIG. 4D depicts a schematic view, along a coronal plane, of the anatomical structures associated with the nasal cavity of the patient of FIG. 4A, with the dilation catheters removed from the patient, and with the nasal septum in a non-deviated state.
Figure 5A:
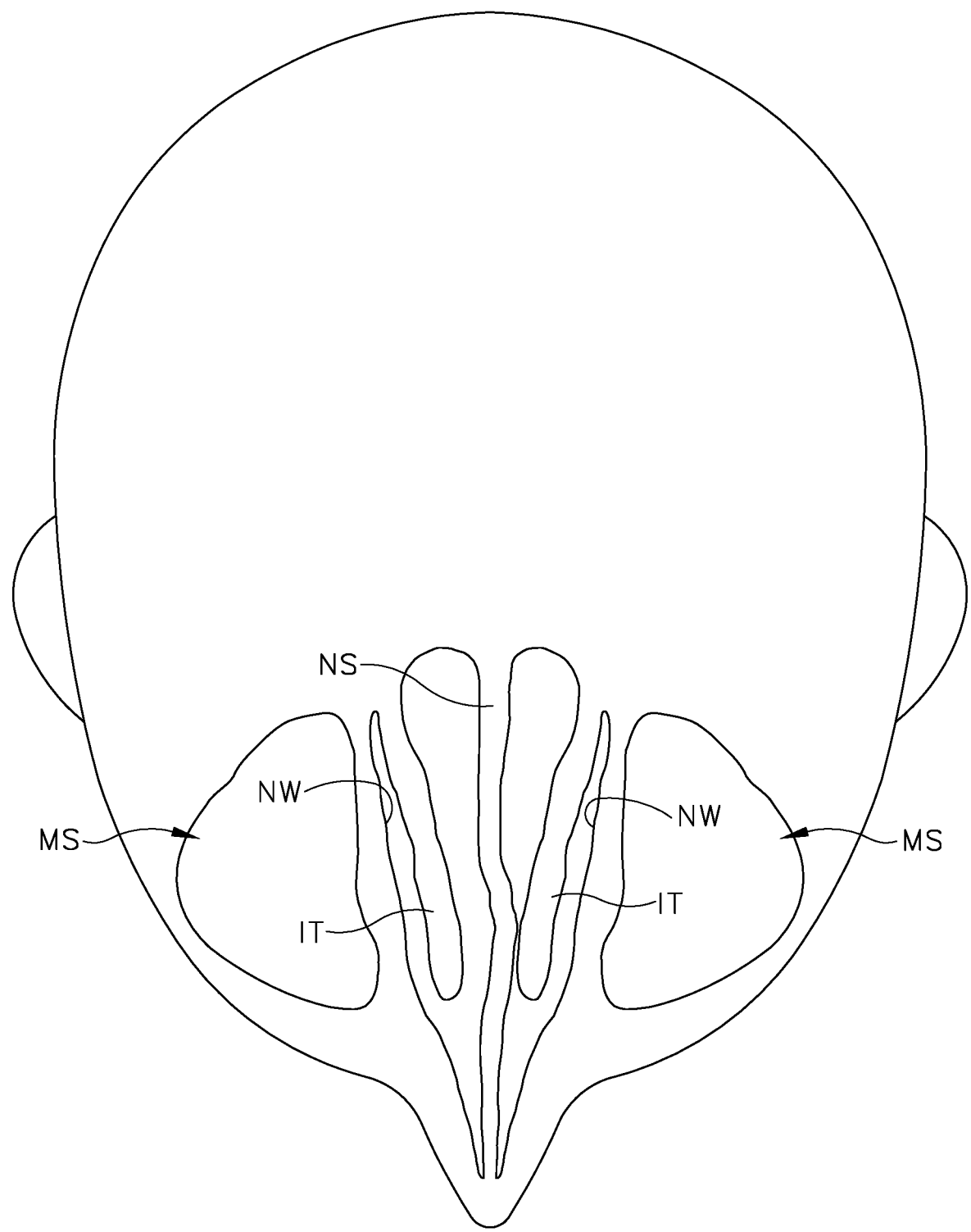
FIG. 5A depicts a schematic view, along an axial plane, of anatomical structures associated with a nasal cavity of a patient, including the nasal septum in the deviated state of FIG. 4A, before the second exemplary treatment procedure.
Figure 5B:
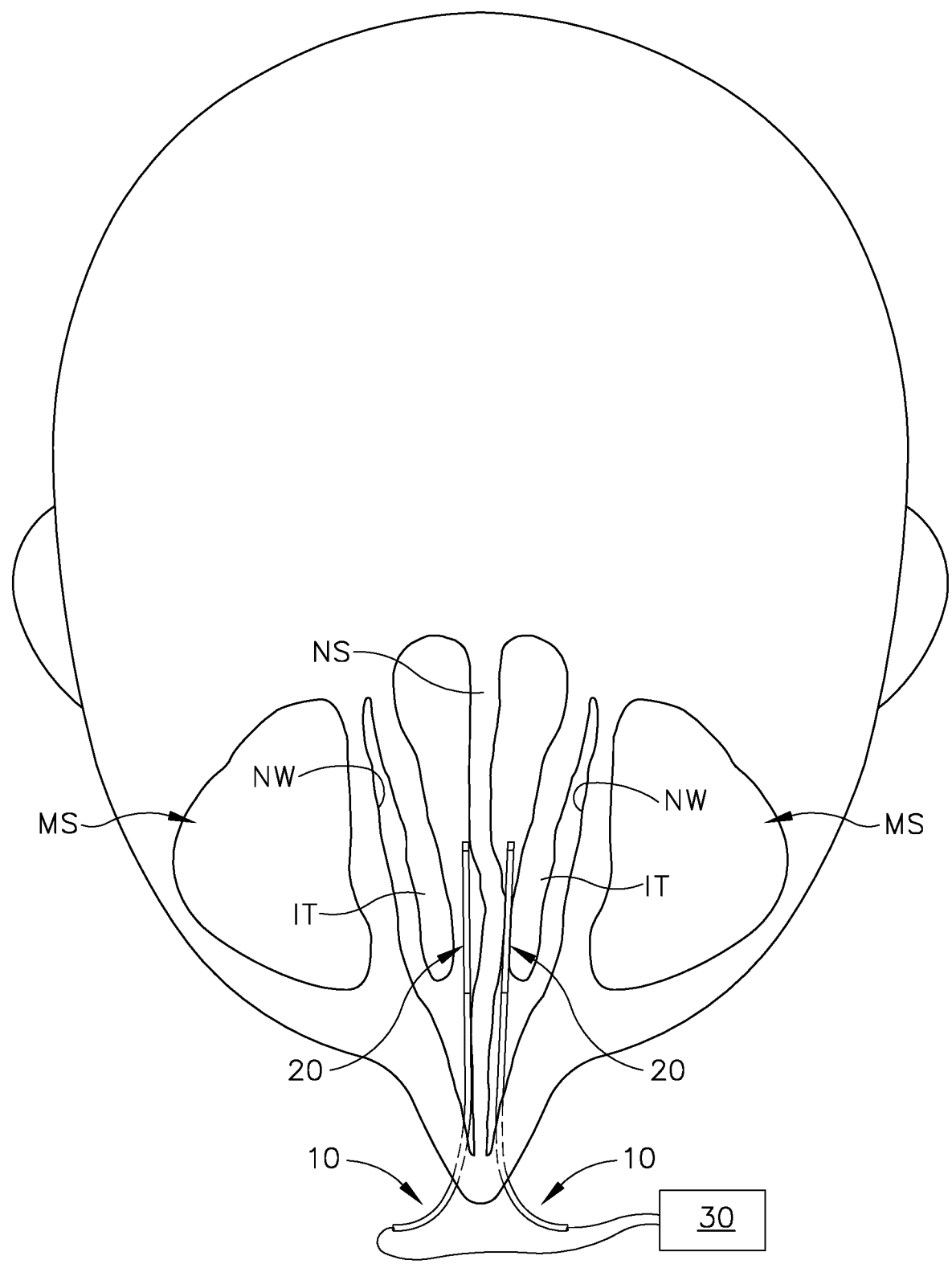
FIG. 5B depicts a schematic view, along an axial plane, of the anatomical structures associated with the nasal cavity of the patient of FIG. 5A, with distal portions of the two dilation catheters inserted through respective nostrils of the patient, and with the dilator of each dilation catheter in the non-expanded state.
Figure 5C:
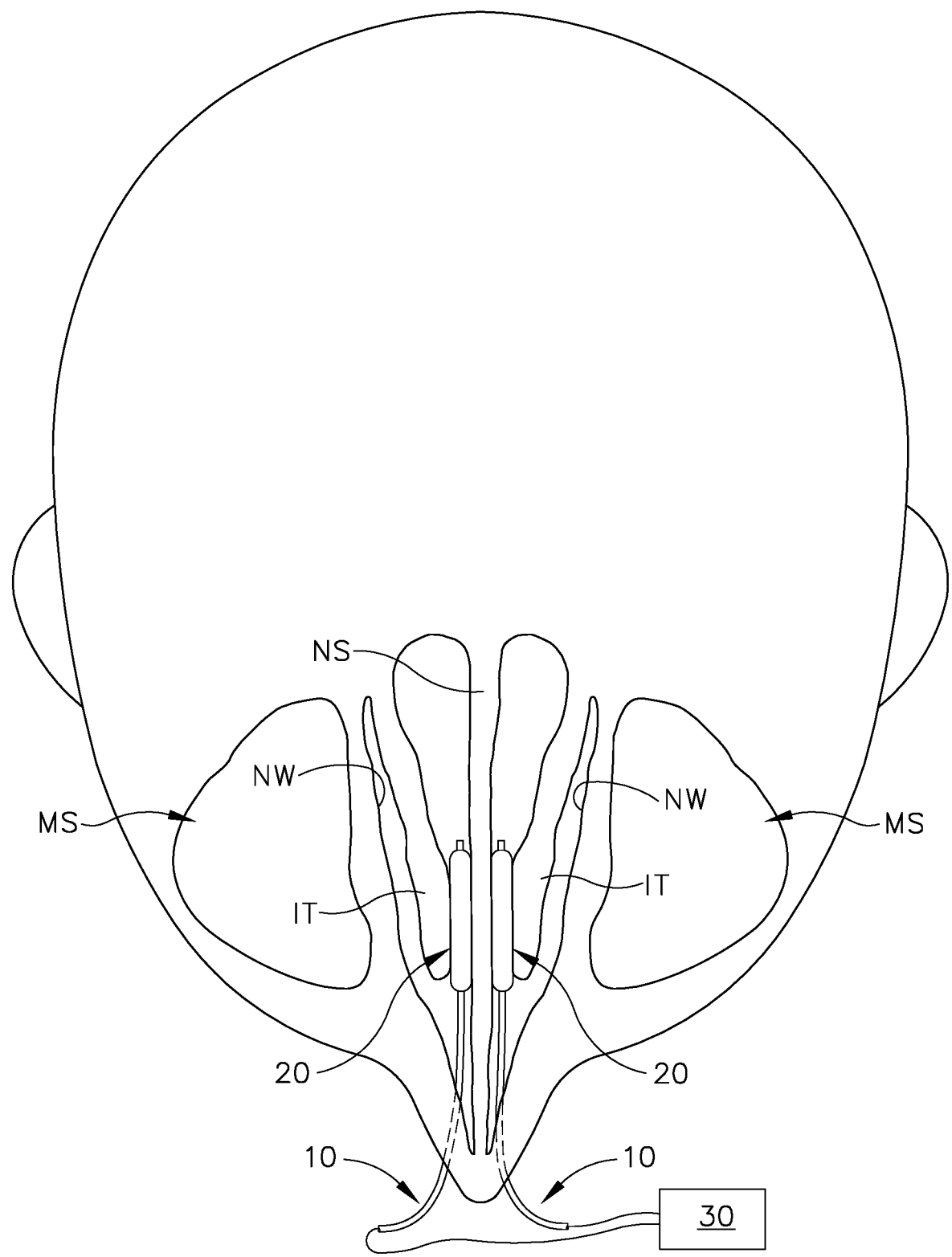
FIG. 5C depicts a schematic view, along an axial plane, of the anatomical structures associated with the nasal cavity of the patient of FIG. 5A, with distal portions of the two dilation catheters inserted through respective nostrils of the patient, and with the dilator of each dilation catheter in the expanded state.
Figure 5D:
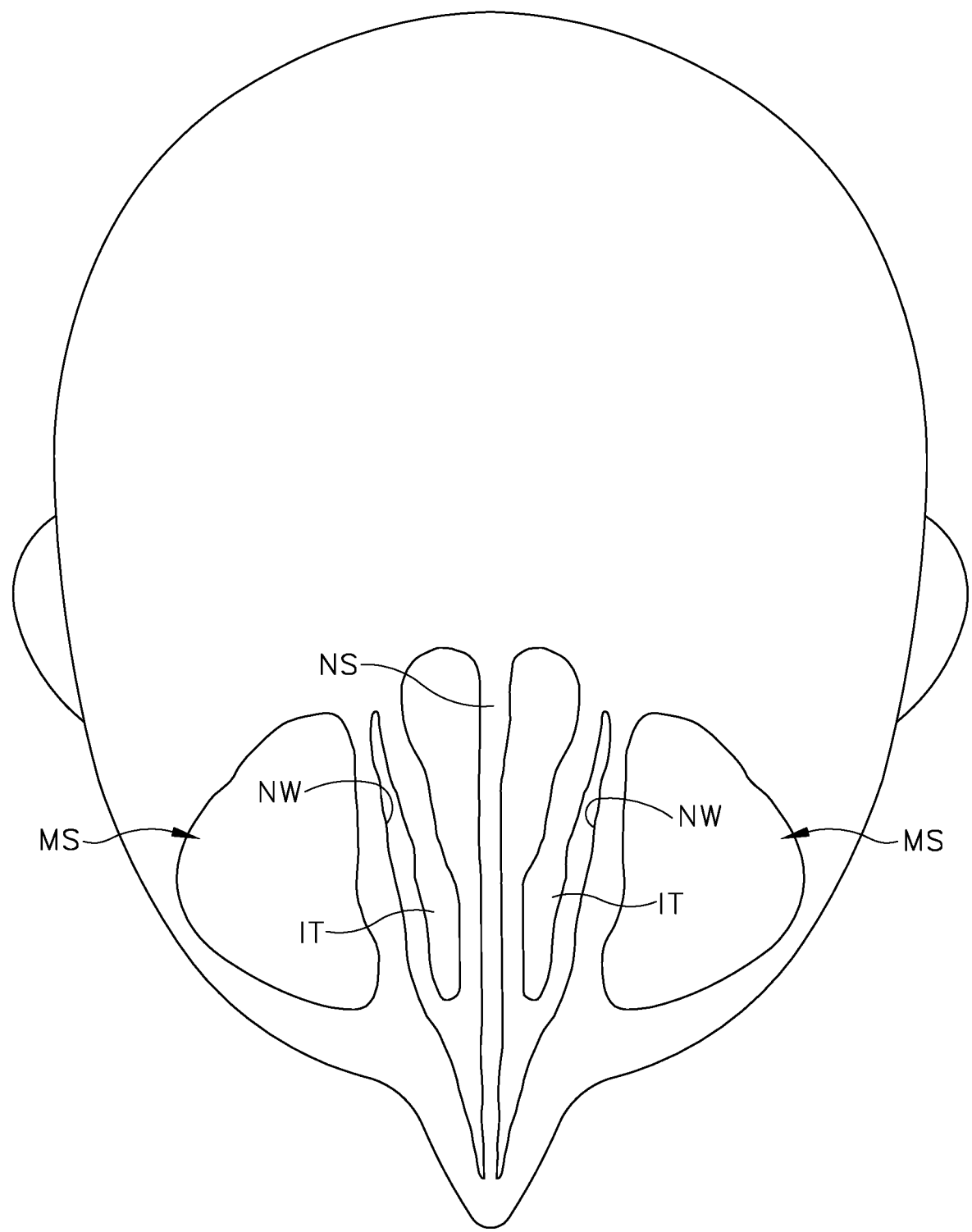
FIG. 5D depicts a schematic view, along an axial plane, of the anatomical structures associated with the nasal cavity of the patient of FIG. 5A, with the dilation catheters removed from the patient, and with the nasal septum in a non-deviated state.

Once dilators (20) have been suitably positioned as shown in FIGS. 4B and 5B, inflation fluid is driven from fluid source (30) to dilators (20), thereby expanding dilators (20) to the expanded state shown in FIGS. 4C and 5C. In the present example, both dilators (20) are expanded simultaneously. In some other versions, the dilator (20) on the left in the view shown in FIGS. 4B and 5B (i.e., the patient's right side) is expanded first; followed by the dilator (20) on the right in the view shown in FIGS. 4B and 5B (i.e., the patient's left side). Also in the present example, both dilators (20) are coupled with the same fluid source (30). In some other versions, each dilator (20) has its own respective fluid source (30). In either case, as the dilator (20) on the right in the view shown in FIGS. 4B and 5B (i.e., the patient's left side) expands, dilator urges the nasal septum (NS) medially, thereby substantially straightening the nasal septum (NS). As the nasal septum (NS) is urged medially, the bone in the nasal septum (NS) may fracture and/or the cartilage in the nasal septum (NS) may plastically deform, such that the medially urged nasal septum (NS) is effectively remodeled and maintains a substantially straight configuration after dilation catheter (10) is removed as shown in FIGS. 4D and 5D.

In the present example, the expanded dilator (20) on the left side in the view shown in FIGS. 4C and 5C (i.e., the patient's right side) may provide a stop for the medialized nasal septum (NS), thereby preventing over-medialization of the nasal septum (NS). In other words, in some scenarios where a procedure is performed as shown in FIGS. 2A-3D with just one dilator (20), dilator (20) may urge the nasal septum (NS) too far medially, to the point where the nasal septum (NS) is transitioned from deviating too far to the patient's left side to deviating too far to the patient's right side, when the goal of the procedure is to achieve a substantially straight nasal septum (NS). Thus, by providing an opposing expanded dilator (20) as shown in FIGS. 4C and 5C, the expanded dilator (20) on the patient's right side may prevent the nasal septum (NS) from being deformed right-of-center by the expanded dilator (20) on the patient's left side. In other words, using two opposing dilators (20) on opposing sides of the nasal septum (NS) may ensure that the nasal septum (NS) is not deformed beyond the substantially straight position shown in FIGS. 4D and 5D. Using two opposing dilators (20) on opposing sides of the nasal septum (NS) may also increase the effect that dilator (20) has on reducing mucosal hypertrophy.

Figure 6:
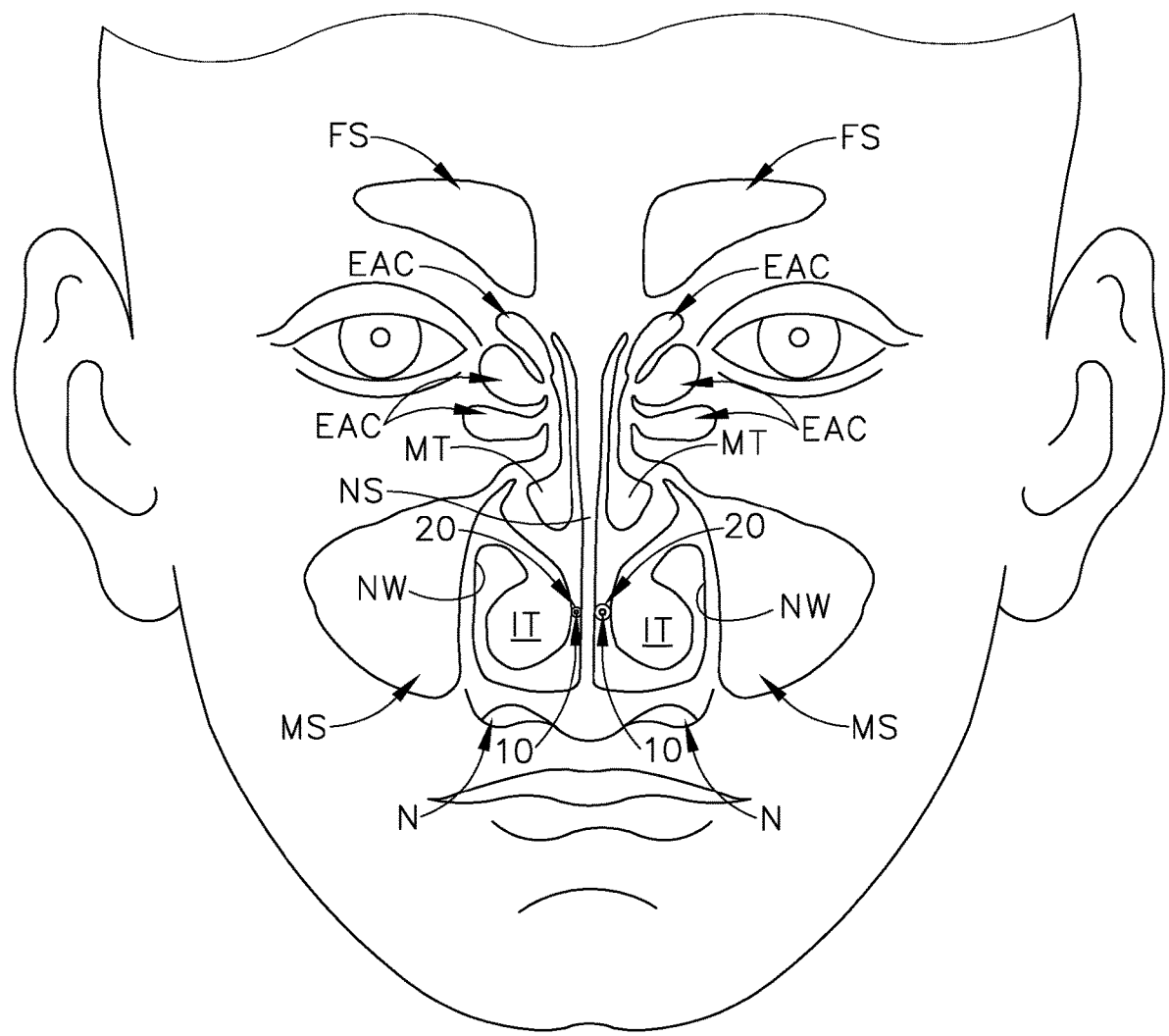
FIG. 6 depicts a schematic view, along a coronal plane, of the anatomical structures associated with the nasal cavity of the patient of FIG. 5A, with distal portions of two alternative dilation catheters inserted through respective nostrils of the patient, and with the dilator of each dilation catheter in the expanded state at different respective outer diameters.

In the example shown in FIGS. 4C and 5C, both dilators (20) are expanded to approximately the same outer diameter. In some other versions, dilators (20) are expanded to different outer diameters, as shown in FIG. 6. By way of example only, in some variations the dilator (20) on the side to which the nasal septum (NS) is deviated (i.e., the patient's left side in the views shown in FIGS. 4A-5D) may be expanded to a larger outer diameter; while the dilator (20) on the opposite side (i.e., the patient's left side in the views shown in FIGS. 4A-5D) may be expanded to a smaller outer diameter). By way of further example only, the larger outer diameter may be approximately 16 mm while the smaller outer diameter may be approximately 10 mm.

Figure 7:
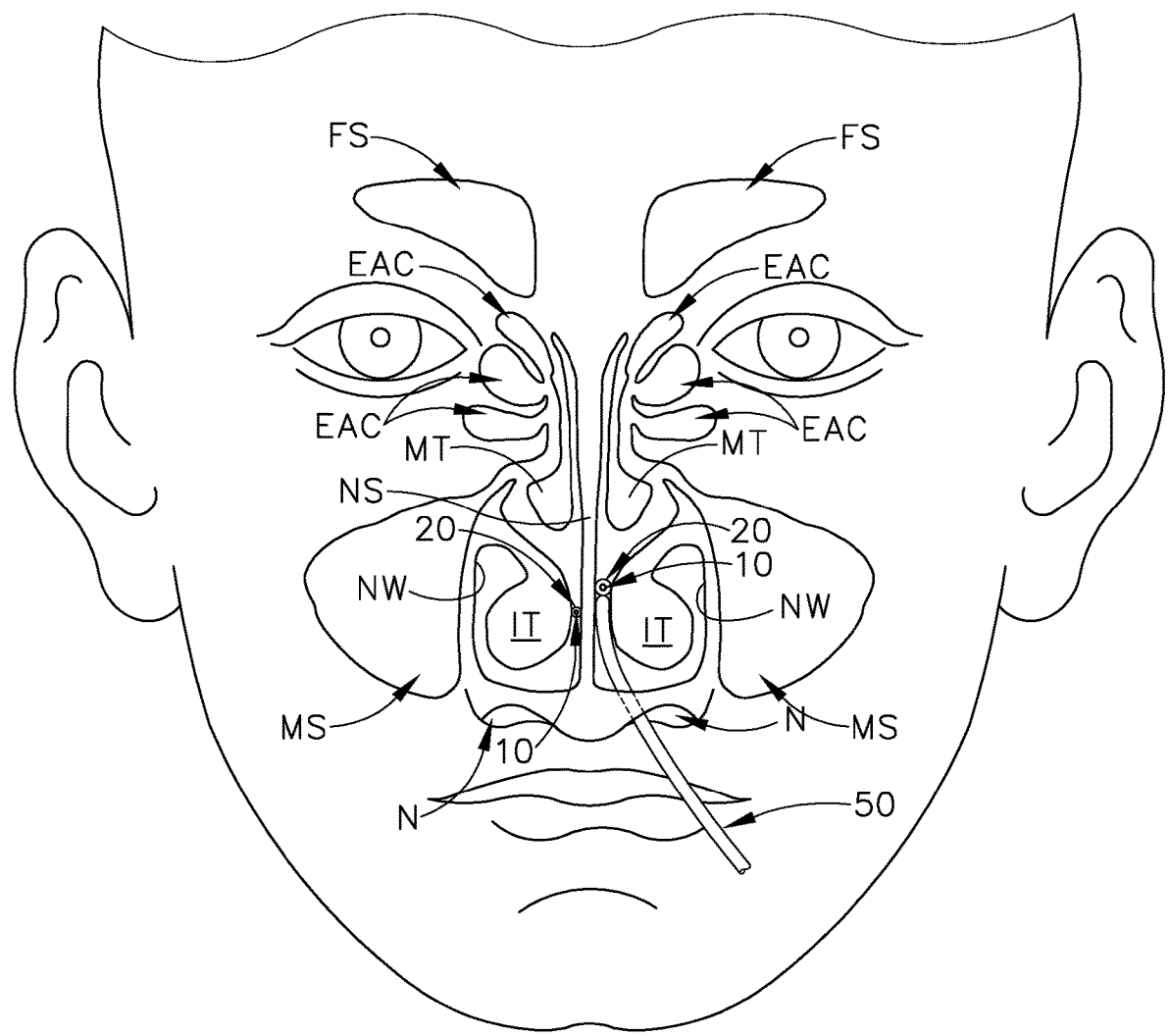
FIG. 7 depicts a schematic view, along a coronal plane, of the anatomical structures associated with the nasal cavity of the patient of FIG. 5A, with distal portions of two alternative dilation catheters inserted through respective nostrils of the patient, with the dilator of each dilation catheter in the expanded state, and with one dilator being pushed to a higher vertical position than the other dilator.

As another merely illustrative variation, dilators (20) may be positioned at different vertical heights within the nasal cavity. For instance, a spacer device (50) may be inserted into a nostril and be used to urge a dilator (20) superiorly, with the dilator (20) on the other side of the nasal septum (NS) being positioned inferiorly relative to the superiorly raised dilator (20). A merely illustrative example of such positioning is shown in FIG. 7. Various suitable forms that spacer device (50) may take will be apparent to those of ordinary skill in the art in view of the teachings herein.

In many of the foregoing examples, the nasal septum (NS) is laterally deviated near the inferior turbinate (IT), such that dilation catheter (10) is positioned to locate dilator (20) between the nasal septum (NS) and the inferior turbinate (IT). In some other scenarios, the nasal septum (NS) laterally deviated near the middle turbinate (MT). In such scenarios, the dilation catheter (10) may be positioned to locate dilator (20) between the nasal septum (NS) and the middle turbinate (MT). Likewise, the dilation catheter (10) may be positioned to locate dilator (20) between the nasal septum (NS) and the superior turbinate (not shown) in scenarios where the nasal septum (NS) is laterally deviated near the superior turbinate.

While the foregoing examples are provided in the context of treating a deviated nasal septum (NS), the procedures identified above may be modified to treat other conditions within the nasal cavity. For instance, dilation catheter (10) may be used to remodel an enlarged turbinate (MT, IT), by placing dilator (20) against the enlarged turbinate (MT, IT) and then expanding dilator (20) to remodel the enlarged turbinate (MT, IT). In such procedures, depending on which side of the turbinate (MT, IT) the dilator (20) is positioned, the lateral nasal wall (NW) or the nasal septum (NS) may provide a mechanical ground for the expanding dilator (20). In such procedures where the nasal septum (NS) is used to provide a mechanical ground, including cases where the nasal septum (NS) is not deviated at all, it may be advantageous to provide an opposing dilator (20) on the opposite side of the nasal septum (NS). This may help shore up the nasal septum (NS) and thereby prevent undesired remodeling of the nasal septum (NS) when the nasal septum (NS) is used to provide a mechanical ground in a procedure for remodeling a turbinate (MT, IT) with a dilator (20).

In addition to, or as an alternative to, remodeling the nasal septum (NS) and/or a turbinate (MT, IT), an expanded dilator (20) may move and/or remodel mucosal tissue in the nasal cavity, which may further promote better airflow through the nasal cavity. For instance, as noted above, an expanded dilator (20) may crush the mucosal tissue that lines a passageway within the nasal cavity, thereby providing a wider pathway for airflow through that passageway.

Figure 8A:
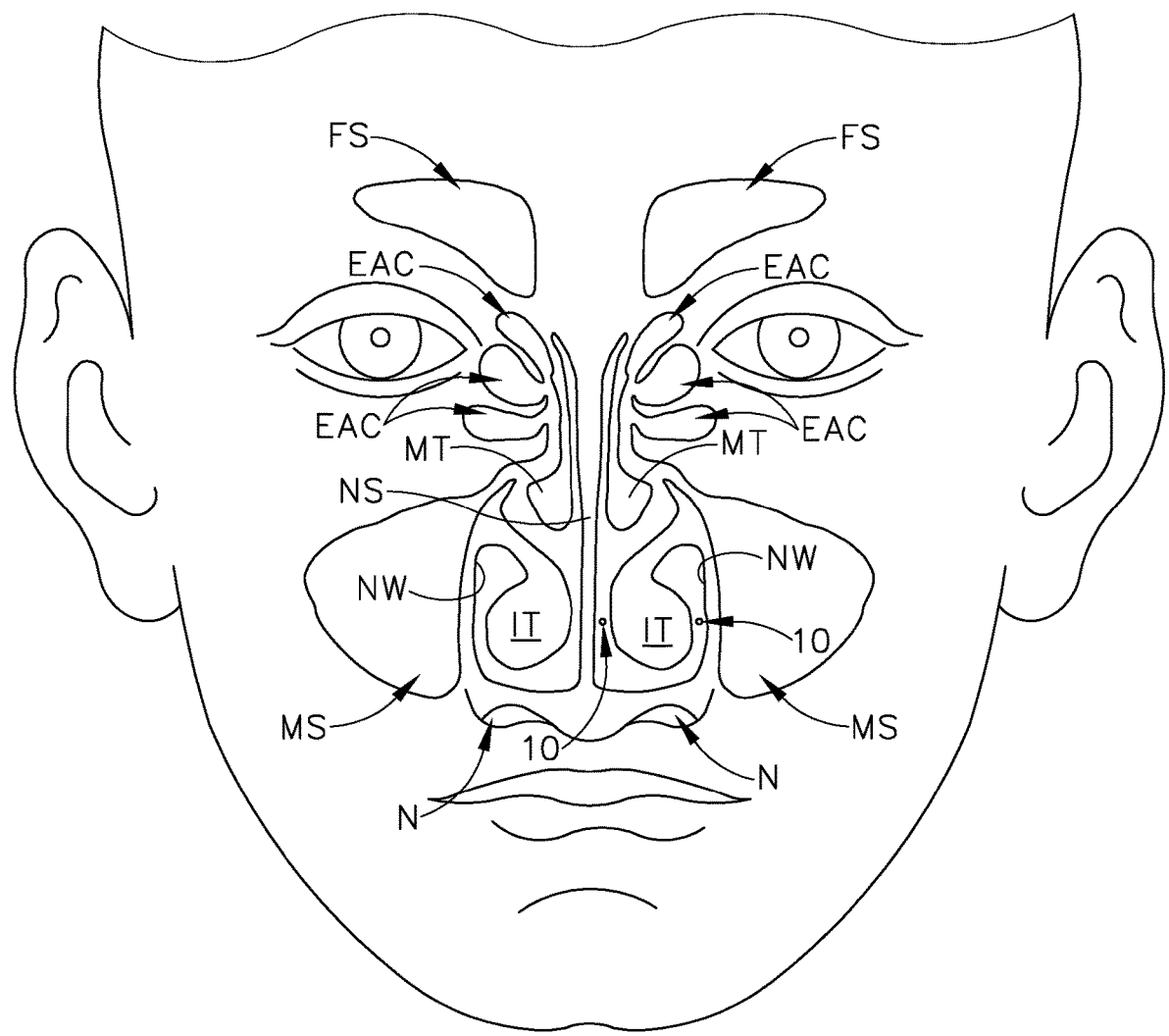
FIG. 8A depicts a schematic view, along a coronal plane, of anatomical structures associated with a nasal cavity of a patient, with a first dilation catheter positioned between an inferior turbinate and the nasal septum, with a second dilation catheter positioned between the inferior turbinate and the lateral nasal wall, and with dilators of both dilation catheters in the non-expanded state.
Figure 8B:
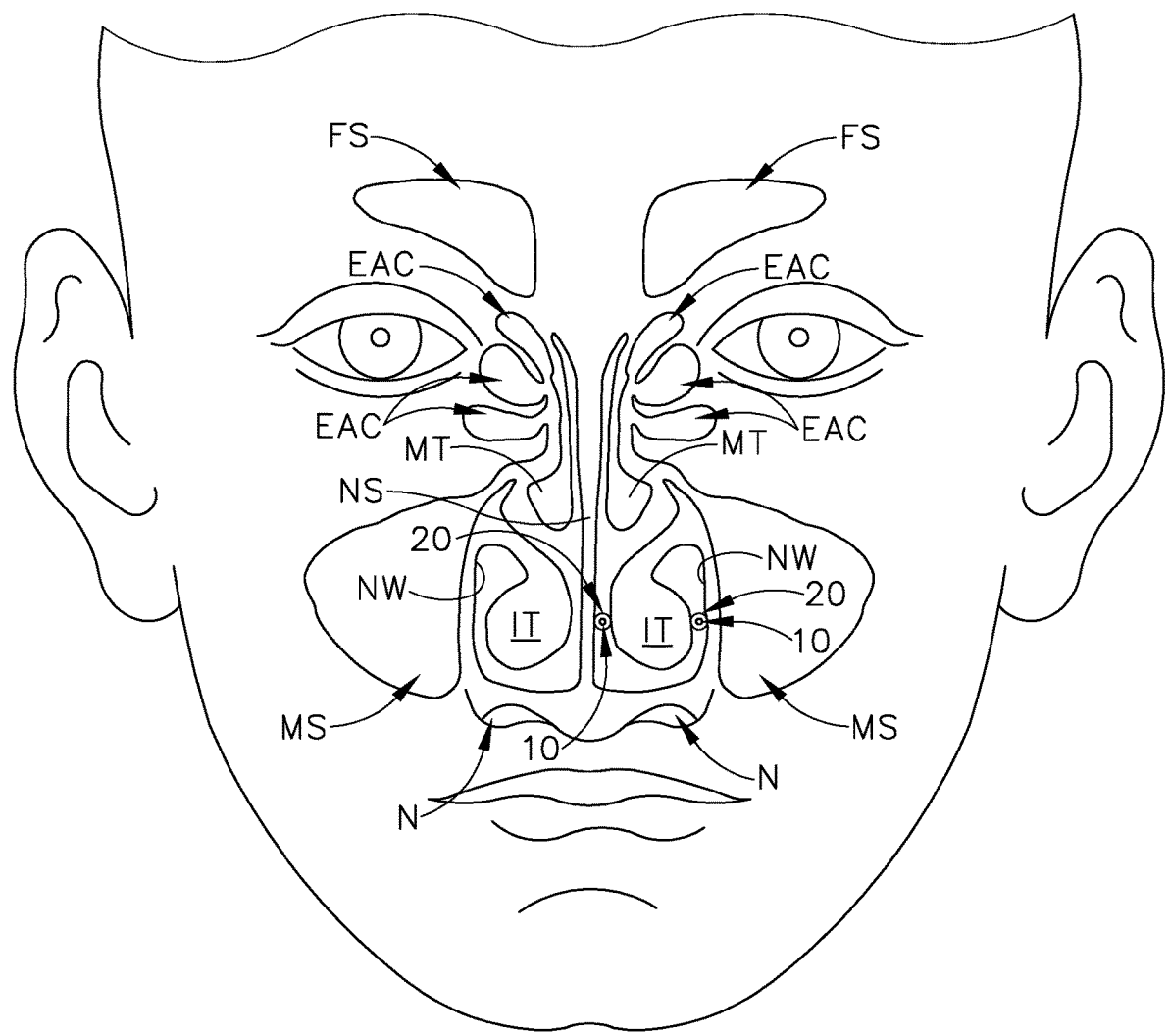
FIG. 8B depicts a schematic view, along a coronal plane, of anatomical structures associated with a nasal cavity of a patient of FIG. 8A, with the first dilation catheter positioned between the inferior turbinate and the nasal septum, with the second dilation catheter positioned between the inferior turbinate and the lateral nasal wall, and with dilators of both dilation catheters in the expanded state.
Figure 9A:
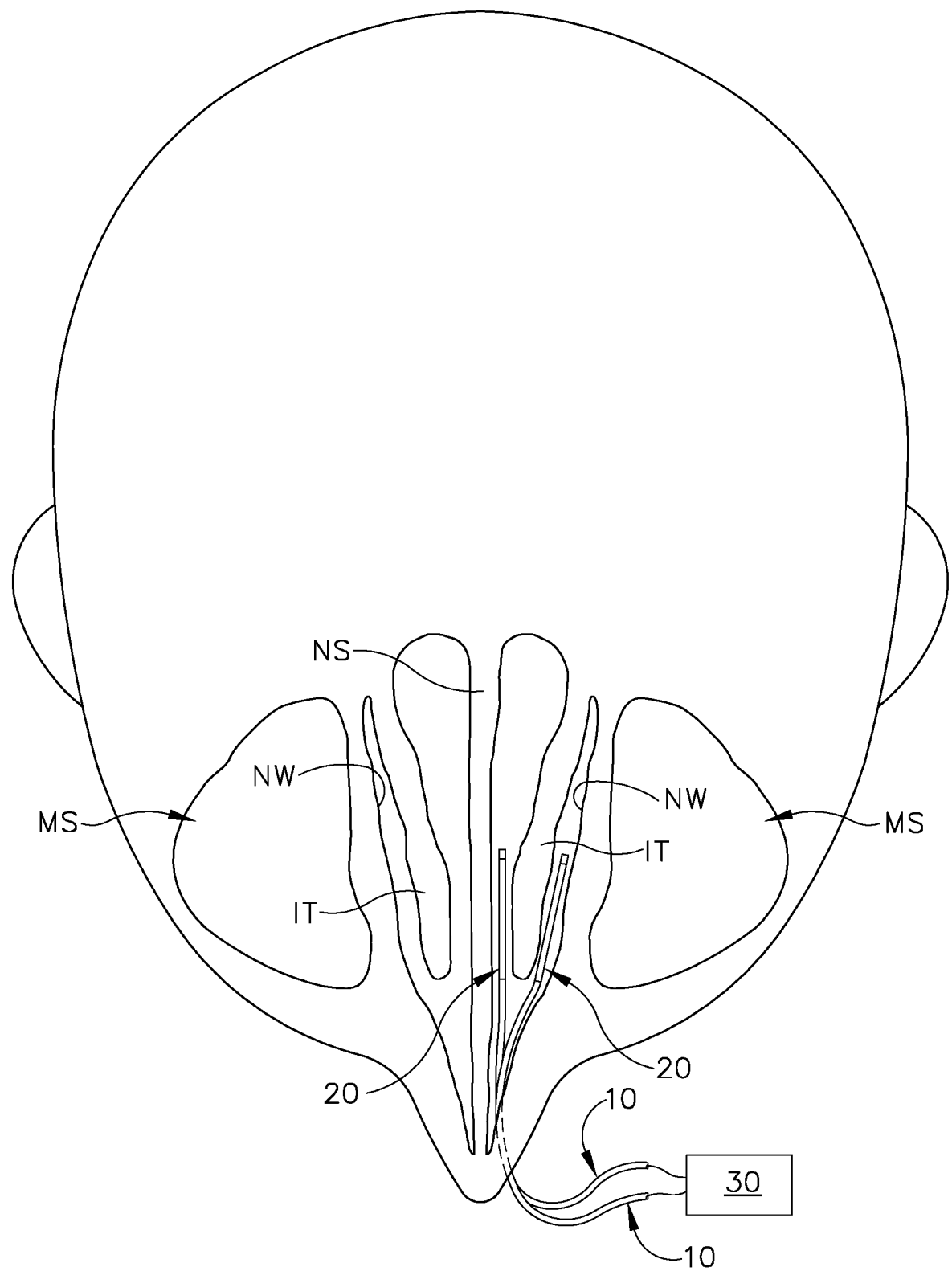
FIG. 9A depicts a schematic view, along an axial plane, of the anatomical structures associated with the nasal cavity of the patient of FIG. 8A, with the first dilation catheter positioned between the inferior turbinate and the nasal septum, with the second dilation catheter positioned between the inferior turbinate and the lateral nasal wall, and with dilators of both dilation catheters in the non-expanded state.
Figure 9B:
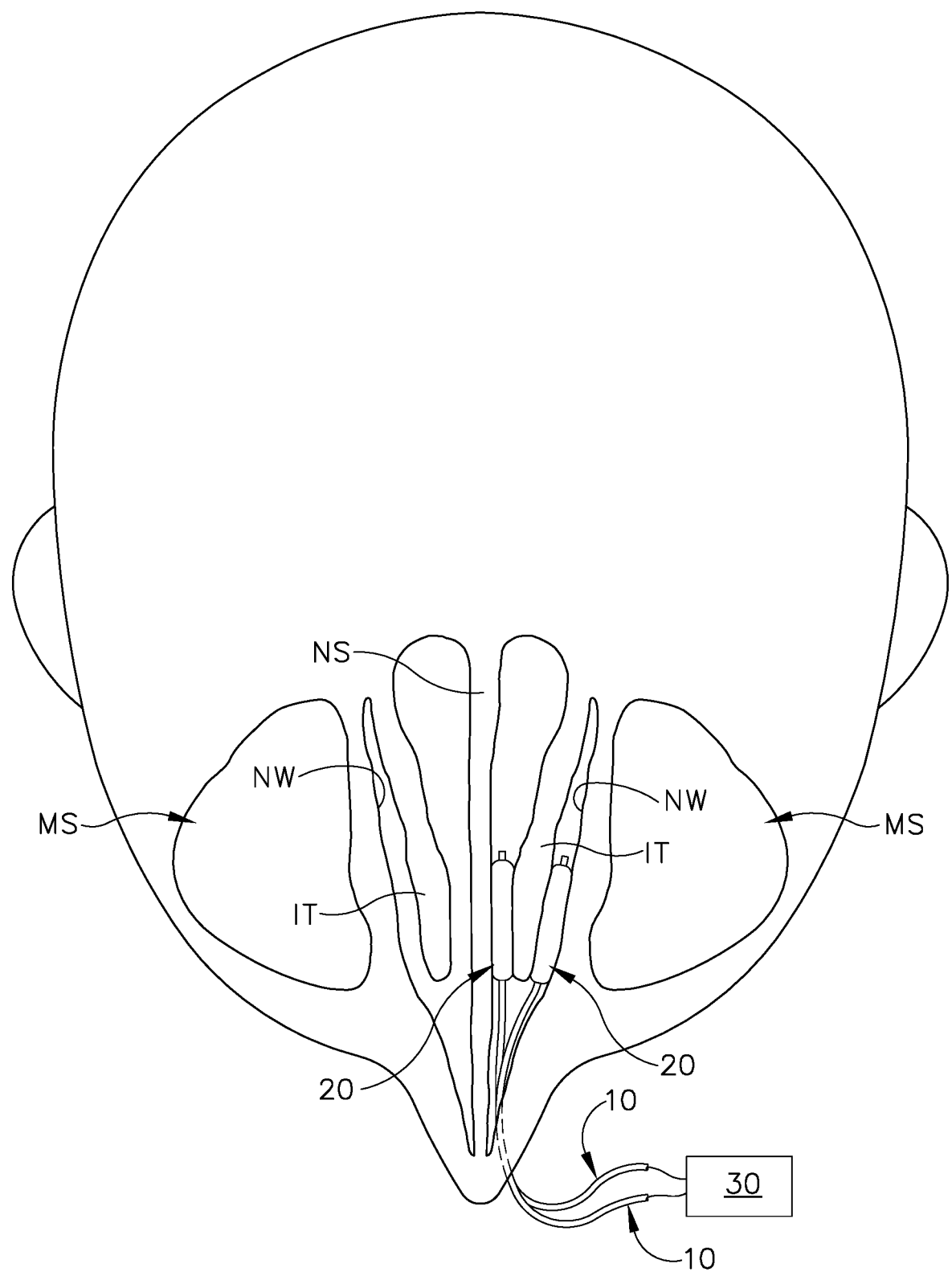
FIG. 9B depicts a schematic view, along an axial plane, of the anatomical structures associated with the nasal cavity of the patient of FIG. 8A, with the first dilation catheter positioned between the inferior turbinate and the nasal septum, with the second dilation catheter positioned between the inferior turbinate and the lateral nasal wall, and with dilators of both dilation catheters in the expanded state.

As yet another merely illustrative example, a first dilator (20) may be positioned between the nasal septum (NS) and the inferior turbinate (IT), with a second dilator (20) being positioned between the inferior turbinate (IT) and the lateral nasal wall (NW) (e.g., in the inferior nasal meatus) as shown in FIGS. 8A and 9A. When these dilators (20) are expanded simultaneously as shown in FIGS. 8B and 9B, this may prevent or otherwise reduce fracturing of bone within the inferior turbinate (IT), while still providing crushing of the mucosa of the inferior turbinate (IT). In some implementations of this procedure, the dilator (20) that is positioned between the inferior turbinate (IT) and the lateral nasal wall (NW) is expanded to an outer diameter that is smaller than the outer diameter to which the dilator (20) between the nasal septum (NS) and the inferior turbinate (IT) is expanded.

In the present example, both dilators (20) are expanded to substantially the same outer diameter at the stage shown in FIGS. 8B and 9B. Alternatively, dilators (20) may be expanded to different outer diameters at the stage shown in FIGS. 8B and 9B. By way of example only, the dilator (20) that is positioned between the inferior turbinate (IT) and the lateral nasal wall (NW) may be expanded to an outer diameter of approximately 10 mm; and the dilator (20) that is positioned between the nasal septum (NS) and the inferior turbinate (IT) may be expanded to an outer diameter of approximately 16 mm. This procedure (and any other procedure directed to treatment of the inferior turbinate (IT) and/or mucosal tissue) may be performed in cases where the patient does not have a deviated nasal septum (NS). Thus, the procedures described herein are not limited to scenarios where the patient has a deviated nasal septum (NS).

III. Exemplary Alternative Dilation Catheters

In some instances, when dilator (20) is inflated in accordance with the description above, dilator (20) may "slip" or otherwise move relative to adjacent anatomical structures in response to contact between dilator (20) and adjacent anatomical structures. If dilator (20) "slips" in response to contact with adjacent anatomical structures during inflation, dilator (20) may not be located in the desired location when fully inflated. If dilator (20) slips during inflation, dilator (20) may thus fail to suitably dilate the targeted anatomical structure. It may therefore be desirable to modify dilator (20) to prevent dilator (20) from slipping relative to adjacent anatomical structure during inflation. Adding a textured outer surface, a non-circular cross-sectional profile, and/or some other kind of friction enhancing feature to dilator (20) may help prevent dilator (20) from slipping relative to adjacent anatomical structures as dilator (20) comes into contact with adjacent anatomical structures during inflation.

Figure 11:
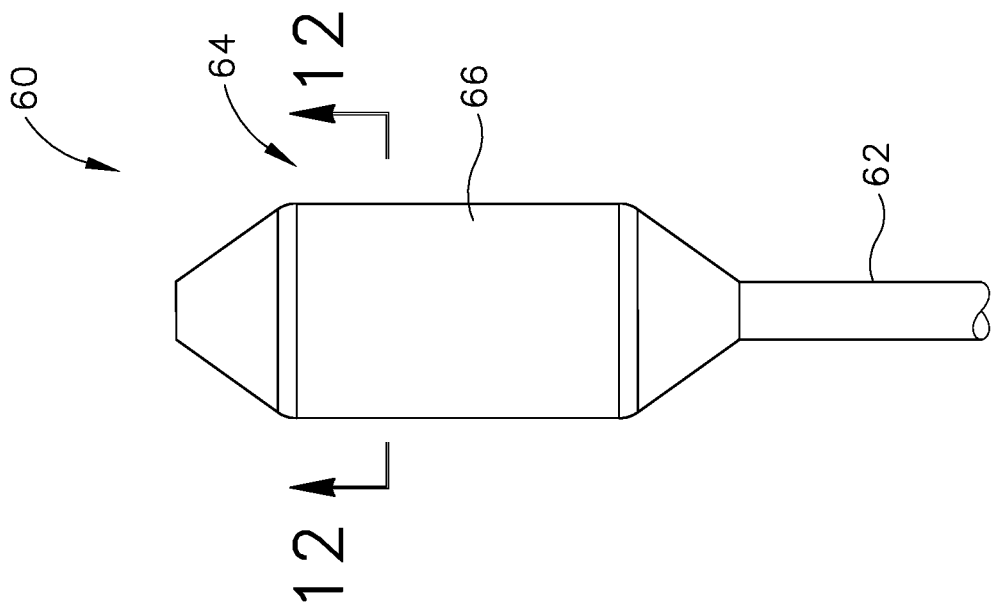
FIG. 11 depicts a side plan view of an exemplary dilation catheter, with a dilator of the dilation catheter in an expanded state.
Figure 10:
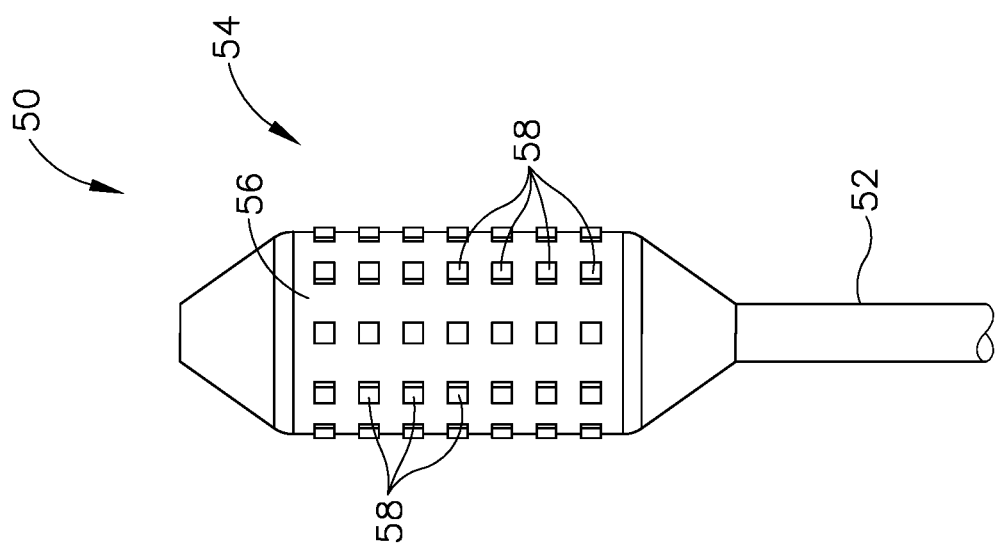
FIG. 10 depicts a side plan view of an exemplary dilation catheter, with a dilator of the dilation catheter in an expanded state.

FIGS. 10 and 11 show alternative dilation catheters (50, 60) that may be readily used in replacement of dilation catheter (10) described above. Dilation catheters (50, 60) are substantially similar to dilation catheters (10) described above, with differences elaborated below. Dilation catheters (50, 60) include respective elongate shafts (52, 62) and dilators (54, 64), which may be substantially similar to elongate shafts (12) and dilator (20) described above, with differences described below. As will be described in greater detail below, each dilator (54, 64) includes a friction enhanced feature configured to prevent slipping of dilators (54, 64) during inflation.

Dilator (54) includes a primary exterior surface (56) and a plurality of secondary protrusions (58) extending from primary exterior surface (56). Primary exterior surface (56) may form a portion of dilator (54) that is substantially similar to dilator (20) described above, while secondary protrusions (58) may create a textured or patterned surface that may help prevent dilator (54) from slipping during inflation. Secondary protrusions (58) may be formed of a material that is different from primary exterior surface (56). Specifically, secondary protrusions (58) may be formed of a "rougher" material that has a greater coefficient of friction compared to primary exterior surface (56). The increased coefficient of friction of secondary protrusions (58) may help prevent dilator (54) from slipping relative to adjacent anatomical structures during inflation in exemplary use. Alternatively, secondary protrusions (58) may be made from the same material of primary exterior surface (56), and the geometry of secondary protrusions (58) may help increase to frictional gripping of dilator (54) with adjacent anatomical structures.

Dilator (64) includes a textured external surface (66) formed of a "rougher" material, such as a rough silicone surface. The roughened surface of textured external surface (66) may provide an increased coefficient of friction compared to dilator (20) described above. This increase in the coefficient of friction may help prevent dilator (64) from slipping relative to adjacent anatomical structures during inflation in exemplary use.

FIGS. 12A-12C show various cross-sectional profiles that may be readily incorporated into dilators (20, 54, 64) in order to help prevent slippage of dilators (20, 54, 64) during inflation. FIG. 12A shows a substantially oval profile (70). FIG. 12B shows a rectangular profile (72) having rounded corners (74). FIG. 12C shows a triangular profile (76) having rounded corners (78). The change in cross-sectional profile, compared to a circular profile, may help prevent dilators (20, 54, 64) from slipping during inflation by limiting points of contact between dilators (20, 54, 64) and adjacent anatomical structures.

In addition to the foregoing, dilators (20, 54, 64) may be constructed and operable in accordance with at least some of the teachings of U.S. Pat. Pub. No. 2014/0277071, entitled "Features to Enhance Grip of Balloon Within Airway," published Sep. 18, 2014, now abandoned, the disclosure of which is incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method comprising: (a) inserting a first dilation catheter into a first nostril of a patient; (b) positioning a first dilator of the first dilation catheter between a nasal septum of the patient and a turbinate of the patient; (c) expanding the first dilator, thereby remodeling two or more of the nasal septum, the turbinate, or mucosal tissue of the patient; and (d) removing the first dilation catheter from the first nostril of the patient.

Example 2

The method of Example 1, wherein the nasal septum is deviated before the act of inserting the first dilation catheter, wherein the nasal septum is substantially straightened after the act of removing the first dilation catheter.

Example 3

The method of any one or more of Examples 1 through 2, wherein the first dilator comprises a balloon, wherein the act of expanding the first dilator comprises communicating an inflation fluid to the balloon.

Example 4

The method of any one or more of Examples 1 through 3, wherein the act of expanding the first dilator comprises medializing the nasal septum.

Example 5

The method of any one or more of Examples 1 through 4, wherein the act of expanding the first dilator comprises lateralizing the turbinate.

Example 6

The method of any one or more of Examples 1 through 5, wherein the turbinate comprises an inferior turbinate.

Example 7

The method of any one or more of Examples 1 through 6, wherein the expanded first dilator comprises a friction enhancing feature.

Example 8

The method of any one or more of Examples 1 through 7, wherein the act of remodeling two or more of the nasal septum, the turbinate, or mucosal tissue of the patient comprises fracturing one or both of bone or cartilage in the nasal septum.

Example 9

The method of any one or more of Examples 1 through 8, wherein the act of remodeling two or more of the nasal septum, the turbinate, or mucosal tissue of the patient comprises fracturing bone in the turbinate.

Example 10

The method of any one or more of Examples 1 through 9, further comprising: (a) inserting a second dilation catheter into a second nostril of the patient; (b) positioning a second dilator of the second dilation catheter adjacent to the nasal septum of the patient; (c) expanding the second dilator; and (d) removing the second dilator from the second nostril of the patient.

Example 11

The method of Example 10, wherein the act of positioning the second dilator comprises positioning the second dilator at a depth corresponding to a depth of the positioned first dilator, such that the first and second dilators are at corresponding depths on opposite sides of the nasal septum.

Example 12

The method of any one or more of Examples 10 through 11, wherein the first and second dilators are expanded simultaneously.

Example 13

The method of Example 12, wherein the first and second dilators exert opposing medial forces on the nasal septum.

Example 14

The method of Example 13, wherein the expanded first dilator urges the nasal septum medially from a deviated configuration toward a substantially straight configuration, wherein the expanded second dilator prevents over-medialization of the nasal septum by the expanded first dilator.

Example 15

The method of any one or more of Examples 10 through 14, wherein the first and second dilators are inflatable, wherein the act of expanding the first dilator comprises communicating inflation fluid from an inflation fluid source to the first dilator, wherein the act of expanding the second dilator comprises communicating inflation fluid from the inflation fluid source to the second dilator.

Example 16

A method comprising: (a) positioning a first dilator adjacent to a first side of a nasal septum in a nasal cavity of a patient; (b) positioning a second dilator adjacent to a second side of the nasal septum; (c) expanding the positioned first dilator; and (d) expanding the positioned second dilator; wherein the expansion of the positioned first dilator urges the nasal septum toward the second dilator, wherein the expansion of the positioned second dilator restricts movement of the urged nasal septum.

Example 17

The method of Example 16, wherein the nasal septum is deviated laterally from a central plane before the acts of positioning the first and second dilators, wherein the expanded first dilator urges the nasal septum medially toward the central plane.

Example 18

The method of Example 17, wherein the expanded second dilator prevents movement of the medialized nasal septum past the central plane.

Example 19

A method comprising: (a) inserting a first dilation catheter into a first nostril of a patient; (b) positioning a first dilator of the first dilation catheter between a first side of a deviated nasal septum of the patient and a turbinate of the patient; (c) inserting a second dilation catheter into a second nostril of the patient; (d) positioning a second dilator of the second dilation catheter adjacent to a second side of the deviated nasal septum of the patient; (e) expanding the positioned first dilator to medialize the deviated nasal septum and thereby remodeling the deviated nasal to achieve a substantially straight configuration of the nasal septum; and (f) expanding the positioned second dilator to restrict movement of the nasal septum beyond the substantially straight configuration.

Example 20

The method of Example 19, wherein expanding the positioned first dilator further lateralizes the turbinate of the patient and thereby remodels the turbinate of the patient.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. In some instances, the instrument may be placed in a reprocessing tray (e.g., a metal bin or basket) and then cleaned in a surgical instrument washer. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, steam, hydrogen peroxide vapor (e.g., via a STERRAD sterilization system by Advanced Sterilization Products of Irvine, Calif.), and/or using any other suitable systems or techniques.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method comprising:
    (a) inserting a first dilation catheter into a first nostril of a patient;
    (b) inserting a second dilation catheter into a second nostril of the patient;
    (c) positioning a first dilator of the first dilation catheter between a nasal septum of the patient and a turbinate of the patient;
    (d) positioning a second dilator of the second dilation catheter adjacent to the nasal septum of the patient;

(e) expanding the first dilator, thereby remodeling two or more of the nasal septum, the turbinate, or mucosal tissue of the patient;

(f) expanding the second dilator, wherein the first and second dilators are expanded simultaneously;

(g) removing the first dilation catheter from the first nostril of the patient; and (h) removing the second dilator from the second nostril of the patient.

2. The method of claim 1, wherein the nasal septum is deviated before the act of inserting the first dilation catheter, wherein the nasal septum is substantially straightened after the act of removing the first dilation catheter.

3. The method of claim 1, wherein the first dilator comprises a balloon, wherein the act of expanding the first dilator comprises communicating an inflation fluid to the balloon.

4. The method of claim 1, wherein the act of expanding the first dilator comprises medializing the nasal septum.

5. The method of claim 1, wherein the act of expanding the first dilator comprises lateralizing the turbinate.

6. The method of claim 1, wherein the act of remodeling two or more of the nasal septum, the turbinate, or mucosal tissue of the patient comprises fracturing one or both of bone or cartilage in the nasal septum.

7. The method of claim 1, wherein the act of remodeling two or more of the nasal septum, the turbinate, or mucosal tissue of the patient comprises fracturing bone in the turbinate.

8. The method of claim 1, wherein the act of positioning the second dilator comprises positioning the second dilator at a depth corresponding to a depth of the positioned first dilator, such that the first and second dilators are at corresponding depths on opposite sides of the nasal septum.

9. The method of claim 1, wherein the first and second dilators are inflatable, wherein the act of expanding the first dilator comprises communicating inflation fluid from an inflation fluid source to the first dilator, wherein the act of expanding the second dilator comprises communicating inflation fluid from the inflation fluid source to the second dilator.

10. The method of claim 1, wherein the turbinate comprises an inferior turbinate.

11. The method of claim 1, wherein the first and second dilators exert opposing medial forces on the nasal septum.

12. The method of claim 11, wherein the expanded first dilator urges the nasal septum medially from a deviated configuration toward a substantially straight configuration, wherein the expanded second dilator prevents over-medialization of the nasal septum by the expanded first dilator.

13. The method of claim 1, wherein the two or more of the nasal septum, the turbinate, or mucosal tissue of the patient includes the nasal septum and the mucosal tissue of the patient.

14. A method comprising:
(a) positioning a first dilator between a first side of a nasal septum and a first turbinate in a nasal cavity of a patient;
(b) positioning a second dilator between a second side of the nasal septum and a second turbinate;
(c) expanding the positioned first dilator; and
(d) expanding the positioned second dilator,
wherein expansion of the positioned first dilator urges the nasal septum toward the second dilator,
wherein expansion of the positioned second dilator restricts movement of the urged nasal septum,
wherein expanding the positioned second dilator occurs simultaneously with expanding the positioned first dilator, wherein simultaneously expanding the first and second dilators reduces a likelihood of fracturing bone within the first and second turbinates, while still crushing mucosa of the first and second turbinates.

15. The method of claim 14, wherein the nasal septum is deviated laterally from a central plane before the acts of positioning the first and second dilators, wherein the expanded first dilator urges the nasal septum medially toward the central plane.

16. The method of claim 15, wherein the expanded second dilator prevents movement of the medialized nasal septum past the central plane.

17. A method comprising:
(a) inserting a first dilation catheter into a first nostril of a patient;
(b) positioning a first dilator of the first dilation catheter between a first side of a deviated nasal septum of the patient and a turbinate of the patient;
(c) inserting a second dilation catheter into a second nostril of the patient;
(d) positioning a second dilator of the second dilation catheter adjacent to a second side of the deviated nasal septum of the patient;
(e) expanding the positioned first dilator to medialize the deviated nasal septum, thereby remodeling the deviated nasal septum to achieve a substantially straight configuration of the nasal septum; and
(f) expanding the positioned second dilator to restrict movement of the nasal septum beyond the substantially straight configuration, wherein expanding the positioned second dilator occurs simultaneously with expanding the positioned first dilator.

18. The method of claim 17, wherein expanding the positioned first dilator further lateralizes the turbinate of the patient and thereby remodels the turbinate of the patient.

19. The method of claim 17, wherein simultaneously expanding the first and second dilators reduces a likelihood of fracturing bone within the turbinate, while still crushing mucosa of the turbinate.

20. The method of claim 17, wherein inserting the second dilation catheter into the second nostril of the patient is performed while the first dilation catheter remains inserted in the first nostril of the patient.

* * * * *